United States Patent [19]

Certa et al.

[11] Patent Number: 5,238,836
[45] Date of Patent: Aug. 24, 1993

[54] PLASMODIUM FALCIPARUM MEROZOITE ANTIGEN PEPTIDES

[75] Inventors: Ulrich Certa, Allschwil, Switzerland; Reiner Gentz, Rheinfelden, Fed. Rep. of Germany; Béla Takacs, Aesch, Switzerland

[73] Assignee: Hoffmann-La Roche Inc., Nutley, N.J.

[21] Appl. No.: 167,811

[22] Filed: Mar. 14, 1988

[30] Foreign Application Priority Data

Mar. 19, 1987 [GB] United Kingdom ............... 8706599

[51] Int. Cl.⁵ .............. C12P 21/02; C12P 19/34; C12N 15/00; C12N 7/00; C12N 1/21; C12N 1/16; C12N 1/18; C07H 15/12; C07K 3/00

[52] U.S. Cl. .................. 435/252.3; 435/693; 435/91; 435/172.3; 435/235.1; 435/320.1; 435/252.33; 435/258.2; 536/27; 530/350; 935/12; 935/29; 935/41; 935/56; 935/65; 935/72

[58] Field of Search ............. 435/68, 70, 91, 172.1, 435/172.3, 252.33, 320, 69.1, 69.7; 536/27; 530/350, 300; 935/19, 27, 41, 56, 65, 73, 81

[56] References Cited

U.S. PATENT DOCUMENTS 4,569,794  2/1986  Smith et al. ..................... 260/113
4,735,799  4/1988  Patarrayo ........................ 424/88

FOREIGN PATENT DOCUMENTS 0154454  9/1985  European Pat. Off. .
2154592  9/1985  United Kingdom .

OTHER PUBLICATIONS

Tanake, et al J. Mol. Bio vol. 195 pp. 273-287 (1987).
Lupski et al Science vol. 220 pp. 1285-1287 (1983).
Hall et al Nature vol. 311 pp. 379-382 (1984).
Lyon et al Proc Natl Acad Sci USA vol. 83 pp. 2989-2993 (1986).
Germino et al., Proc. Natl. Acad. Sci. USA 80:6848 (1983).
Hall et al., Mol. Biochem. Parasitol. 7:247 (1983).
Hall et al., Mol. Biochem. Parasitol. 11:61 (1984).
Holder et al., J. Exp. Med. 156:1528 (1982).
Holder et al., Nature 317:270 (1985).
Hopp et al., European Patent Application Publication No. 150 126 (1985).
Macka et al., Enbo J. 4:3823 (1985).
Nilsson et al., Nucleic Acids Res. 13:1151 (1985).
Perrin et al., Clin. Exp. Immunol. 41:91 (1980).
Weber et al., Nucleic Acids Res. 14:3311 (1986).

*Primary Examiner*—Joan Ellis
*Attorney, Agent, or Firm*—George M. Gould; William H. Epstein; Catherine B. Roseman

[57] ABSTRACT

The present invention provides polypeptides having an amino acid sequence derived from the 190 kD precursor to the major merozoite surface antigens of the K1 isolate of *Plasmodium falciparum*. These polypeptides are capable of eliciting an immune response against different isolates of *Plasmodium falciparum*. The invention further provides immunogenic compositions and vaccines containing such polypeptides, antibodies raised against the polypeptides. a DNA sequence coding for one of the polypeptides, a replicable microbial vector containing such a DNA sequence and a microorganism transformed with such a vector. The invention also provides processes for the production of the polypeptides, immunogenic compositions, microorganisms and antibodies of the invention and for the use of the polypeptides and immunogenic compositions for the immunization of mammals against malaria.

12 Claims, 13 Drawing Sheets

Fig. 2

```
              10         20         30         40         50
   0 CCTCGAGGCT GGCATCCCTA ACATATCCGA ATGGTTACTT AAACAACGGA
  50 GGACTAGCGT ATCCCTTCGC ATAGGGTTTG AGTTAGATAA AGTATATGCT
 100 GAACTTTCTT CTTTGCTCAA AGAATCATAA AAAATTTATT TGCTTTCAGG
 150 AAAATTTTTC TGTATAATAG ATTCAAATTG TGAGCGGATA ACAATTTGAA
 200 TTCATTAAAG AGGAGAAATT AAGCATGCGA GGATCCGGCA TCATGGTTCG
 250 ACCATTGAAC TGCATCGTCG CCGTGTCCCA AAATATGGGG ATTGGCAAGA
 300 ACGGAGACCT ACCCTGGCCT CCGCTCAGGA ACGAGTTCAA GTACTTCCAA
 350 AGAATGACCA CAACCTCTTC AGTGGAAGGT AAACAGAATC TGGTGATTAT
 400 GGGTAGGAAA ACCTGGTTCT CCATTCCTGA GAAGAATCGA CCTTTAAAGG
 450 ACAGAATTAA TATAGTTCTC AGTAGAGAAC TCAAAGAACC ACCACGAGGA
 500 GCTCATTTTC TTGCCAAAAG TTTGGATGAT GCCTTAAGAC TTATTGAACA
 550 ACCGGAATTG GCAAGTAAAG TAGACATGGT TTGGATAGTC GGAGGCAGTT
 600 CTGTTTACCA GGAAGCCATG AATCAACCAG GCCACCTTAG ACTCTTTGTG
 650 ACAAGGATCA TGCAGGAATT TGAAAGTGAC ACGTTTTCC CAGAAATTGA
 700 TTTGGGGAAA TATAAACTTC TCCCAGAATA CCCAGGCGTC CTCTCTGAGG
 750 TCCAGGAGGA AAAAGGCATC AAGTATAAGT TTGAAGTCTA CGAGAAGAAA
 800 GACTAACAGG AAGATGCTTT CAAGTTCTCT GCTCCCTCC TAAAGCTATG
 850 CATTTTTATA AGACCATGGG ACTTTTGCTG GCTTTAGATC CGGCCAAGCT
 900 TGGACTCCTG TTGATAGATC CAGTAATGAC CTCAGAACTC CATCTGGATT
 950 TGTTCAGAAC GCTCGGTTGC CGCCGGGCGT TTTTTATTGG TGAGAATCCA
1000 AGCTAGCTTG GCGAGATTTT CAGGAGCTAA GGAAGCTAAA ATGGAGAAAA
1050 AAATCACTGG ATATACCACC GTTGATATAT CCCAATGGCA TCGTAAAGAA
1100 CATTTGAGG CATTTCAGTC AGTTGCTCAA TGTACCTATA ACCAGACCGT
1150 TCAGCTGGAT ATTACGGCCT TTTTAAAGAC CGTAAAGAAA AATAAGCACA
```

Fig. 2 (cont.)

```
          10         20         30         40         50
1200 AGTTTTATCC GGCCTTTATT CACATTCTTG CCCGCCTGAT GAATGCTCAT
1250 CCGGAATTTC GTATGGCAAT GAAAGACGGT GAGCTGGTGA TATGGGATAG
1300 TGTTCACCCT TGTTACACCG TTTTCCATGA GCAAACTGAA ACGTTTTCAT
1350 CGCTCTGGAG TGAATACCAC GACGATTTCC GGCAGTTTCT ACACATATAT
1400 TCGCAAGATG TGGCGTGTTA CGGTGAAAAC CTGGCCTATT TCCCTAAAGG
1450 GTTTATTGAG AATATGTTTT TCGTCTCAGC CAATCCCTGG GTGAGTTTCA
1500 CCAGTTTTGA TTTAAACGTG GCCAATATGG ACAACTTCTT CGCCCCCGTT
1550 TTCACCATGG GCAAATATTA TACGCAAGGC GACAAGGTGC TGATGCCGCT
1600 GGCGATTCAG GTTCATCATG CCGTCTGTGA TGGCTTCCAT GTCGGCAGAA
1650 TGCTTAATGA ATTACAACAG TACTGCGATG AGTGGCAGGG CGGGGCGTAA
1700 TTTTTTTAAG GCAGTTATTG GTGCCCTTAA ACGCCTGGGG TAATGACTCT
1750 CTAGCTTGAG GCATCAAATA AAACGAAAGG CTCAGTCGAA AGACTGGGCC
1800 TTTCGTTTTA TCTGTTGTTT GTCGGTGAAC GCTCTCCTGA GTAGGACAAA
1850 TCCGCCGCTC TAGAGC
                  |
                 2068
```

```
————pBR322——————————————————————————A
                                    |
                                   4358
```

Fig. 4

```
           10         20         30         40         50
   0 CCTCGAGGCT GGCATCCCTA ACATATCCGA ATGGTTACTT AAACAACGGA
  50 GGACTAGCGT ATCCCTTCGC ATAGGGTTTG AGTTAGATAA AGTATATGCT
 100 GAACTTTCTT CTTTGCTCAA AGAATCATAA AAAATTTATT TGCTTTCAGG
 150 AAAATTTTTC TGTATAATAG ATTCAAATTG TGAGCGGATA ACAATTTGAA
 200 TTCATTAAAG AGGAGAAATT AACTATGAGG GGATCCGTCG ACCTGCAGCC
 250 AAGCTTGGAC TCCTGTTGAT AGATCCAGTA ATGACCTCAG AACTCCATCT
 300 GGATTTGTTC AGAACGCTCG GTTGCCGCCG GGCGTTTTTT ATTGGTGAGA
 350 ATCCAAGCTA GCTTGGCGAG ATTTTCAGGA GCTAAGGAAG CTAAAATGGA
 400 GAAAAAAATC ACTGGATATA CCACCGTTGA TATATCCCAA TGGCATCGTA
 450 AAGAACATTT TGAGGCATTT CAGTCAGTTG CTCAATGTAC CTATAACCAG
 500 ACCGTTCAGC TGGATATTAC GGCCTTTTTA AAGACCGTAA AGAAAAATAA
 550 GCACAAGTTT TATCCGGCCT TTATTCACAT TCTTGCCCGC CTGATGAATG
 600 CTCATCCGGA ATTTCGTATG GCAATGAAAG ACGGTGAGCT GGTGATATGG
 650 GATAGTGTTC ACCCTTGTTA CACCGTTTTC CATGAGCAAA CTGAAACGTT
 700 TTCATCGCTC TGGAGTGAAT ACCACGACGA TTTCCGGCAG TTTCTACACA
 750 TATATTCGCA AGATGTGGCG TGTTACGGTG AAAACCTGGC CTATTTCCCT
 800 AAAGGGTTTA TTGAGAATAT GTTTTTCGTC TCAGCCAATC CCTGGGTGAG
 850 TTTCACCAGT TTTGATTTAA ACGTGGCCAA TATGGACAAC TTCTTCGCCC
 900 CCGTTTTCAC CATGGGCAAA TATTATACGC AAGGCGACAA GGTGCTGATG
 950 CCGCTGGCGA TTCAGGTTCA TCATGCCGTC TGTGATGGCT TCCATGTCGG
1000 CAGAATGCTT AATGAATTAC AACAGTACTG CGATGAGTGG CAGGGCGGGG
1050 CGTAATTTTT TTAAGGCAGT TATTGGTGCC CTTAAACGCC TGGGGTAATG
1100 ACTCTCTAGC TTGAGGCATC AAATAAAACG AAAGGCTCAG TCGAAAGACT
1150 GGGCCTTTCG TTTTATCTGT TGTTTGTCGG TGAACGCTCT CCTGAGTAGG
1200 ACAAATCCGC CGCTCTAGAG C─────────────────────────────
                          │
                        2068

────pBR322──────────────────────────────────────A
                                                │
                                              4358
```

Fig. 6

```
          10         20         30         40         50
   0 AAGCTTCACG CTGCCGCAAG CACTCAGGGC GCAAGGGCTG CTAAAGGAAG
  50 CGGAACACGT AGAAAGCCAG TCCGCAGAAA CGGTGCTGAC CCCGGATGAA
 100 TGTCAGCTAC TGGGCTATCT GGACAAGGGA AAACGCAAGC GCAAAGAGAA
 150 AGCAGGTAGC TTGCAGTGGG CTTACATGGC GATAGCTAGA CTGGGCGGTT
 200 TTATGGACAG CAAGCGAACC GGAATTGCCA GCTGGGGCGC CCTCTGGTAA
 250 GGTTGGGAAG CCCTGCAAAG TAAACTGGAT GGCTTTCTTG CCGCCAAGGA
 300 TCTGATGGCG CAGGGGATCA AGATCTGATC AAGAGACAGG ATGAGGATCG
 350 TTTCGCATGA TTGAACAAGA TGGATTGCAC GCAGGTTCTC CGGCCGCTTG
 400 GGTGGAGAGG CTATTCGGCT ATGACTGGGC ACAACAGACA ATCGGCTGCT
 450 CTGATGCCGC CGTGTTCCGG CTGTCAGCGC AGGGGCGCCC GGTTCTTTTT
 500 GTCAAGACCG ACCTGTCCGG TGCCCTGAAT GAACTGCAGG ACGAGGCAGC
 550 GCGGCTATCG TGGCTGGCCA CGACGGGCGT TCCTTGCGCA GCTGTGCTCG
 600 ACGTTGTCAC TGAAGCGGGA AGGGACTGGC TGCTATTGGG CGAAGTGCCG
 650 GGGCAGGATC TCCTGTCATC TCACCTTGCT CCTGCCGAGA AAGTATCCAT
 700 CATGGCTGAT GCAATGCGGC GGCTGCATAC GCTTGATCCG GCTACCTGCC
 750 CATTCGACCA CCAAGCGAAA CATCGCATCG AGCGAGCACG TACTCGGATG
 800 GAAGCCGGTC TTGTCGATCA GGATGATCTG GACGAAGAGC ATCAGGGGCT
 850 CGCGCCAGCC GAACTGTTCG CCAGGCTCAA GGCGCGCATG CCCGACGGCG
 900 AGGATCTCGT CGTGACCCAT GGCGATGCCT GCTTGCCGAA TATCATGGTG
 950 GAAAATGGCC GCTTTTCTGG ATTCATCGAC TGTGGCCGGC TGGGTGTGGC
1000 GGACCGCTAT CAGGACATAG CGTTGGCTAC CCGTGATATT GCTGAAGAGC
1050 TTGGCGGCGA ATGGGCTGAC CGCTTCCTCG TGCTTTACGG TATCGCCGCT
1100 CCCGATTCGC AGCGCATCGC CTTCTATCGC CTTCTTGACG AGTTCTTCTG
1150 AGCGGGACTC TGGGGTTCGA AATGACCGAC CAAGCGACGC CCAACCTGCC

1200 ATCACGAGAT TTCGATTCCA CCGCCGCCTT CTATGAAAGG TTGGGCTTCG
1250 GAATCGTTTT CCGGGACGCC GGCTGGATGA TCCTCCAGCG CGGGGATCTC
1300 ATGCTGGAGT TCTTCGCCCA CCCCGGGCTC GATCCCCTCG CGAGTTGGTT
1350 CAGCTGCTGC CTGAGGCTGG ACGACCTCGC GGAGTTCTAC CGGCAGTGCA
1400 AATCCGTCGG CATCCAGGAA ACCAGCAGCG GCTATCCGCG CATCCATGCC
1450 CCCGAACTGC AGGAGTGGGG AGGCACGATG GCCGCTTTGG TCGACAATTC
1500 GCGCTAACTT ACATTAATTG CGTTGCGCTC ACTGCCCGCT TTCCAGTCGG
1550 GAAACCTGTC GTGCCAGCTG CATTAATGAA TCGGCCAACG CGCGGGGAGA
1600 GGCGGTTTGC GTATTGGGCG CCAGGGTGGT TTTTCTTTTC ACCAGTGAGA
1650 CGGGCAACAG CTGATTGCCC TTCACCGCCT GGCCCTGAGA GAGTTGCAGC
1700 AAGCGGTCCA CGCTGGTTTG CCCCAGCAGG CGAAAATCCT GTTTGATGGT
1750 GGTTAACGGC GGGATATAAC ATGAGCTGTC TTCGGTATCG TCGTATCCCA
1800 CTACCGAGAT ATCCGCACCA ACGCGCAGCC CGGACTCGGT AATGGCGCGC
1850 ATTGCGCCCA GCGCCATCTG ATCGTTGGCA ACCAGCATCG CAGTGGGAAC
```

FIG. 6 (CONT.)

```
         10          20          30          40          50
1900 GATGCCCTCA TTCAGCATTT GCATGGTTTG TTGAAAACCG GACATGGCAC
1950 TCCAGTCGCC TTCCCGTTCC GCTATCGGCT GAATTTGATT GCGAGTGAGA
2000 TATTTATGCC AGCCAGCCAG ACGCAGACGC GCCGAGACAG AACTTAATGG
2050 GCCCGCTAAC AGCGCGATTT GCTGGTGACC CAATGCGACC AGATGCTCCA
2100 CGCCCAGTCG CGTACCGTCT TCATGGGAGA AAATAATACT GTTGATGGGT
2150 GTCTGGTCAG AGACATCAAG AAATAACGCC GGAACATTAG TGCAGGCAGC
2200 TTCCACAGCA ATGGCATCCT GGTCATCCAG CGGATAGTTA ATGATCAGCC
2250 CACTGACGCG TTGCGCGAGA AGATTGTGCA CCGCCGCTTT ACAGGCTTCG
2300 ACGCCGCTTC GTTCTACCAT CGACACCACC ACGCTGGCAC CCAGTTGATC
2350 GGCGCGAGAT TAATCGCCG CGACAATTTG CGACGGCGCG TGCAGGGCCA
2400 GACTGGAGGT GGCAACGCCA ATCAGCAACG ACTGTTTGCC CGCCAGTTGT
2450 TGTGCCACGC GGTTGGGAAT GTAATTCAGC TCCGCCATCG CCGCTTCCAC
2500 TTTTTCCCGC GTTTTCGCAG AAACGTGGCT GGCCTGGTTC ACCACGCGGG
2550 AAACGGTCTG ATAAGAGACA CCGGCATACT CTGCGACATC GTATAACGTT
2600 ACTGGTTTCA CATTCACCAC CCTGAATTGA CTCTCTTCCG GGCGCTATCA
2650 TGCCATACCG CGAAAGGTTT TGCACCATTC GATGGTGTCA ACGTAAATGC
2700 ATGCCGCTTC GCCTTCGCGC GCGAATTGTC GACCCTGTCC CTCCTGTTCA
2750 GCTACTGACG GGGTGGTGCG TAACGGCAAA AGCACCGCCG GACATCAGCG
2800 CTAGCGGAGT GTATACTGGC TTACTATGTT GGCACTGATG AGGGTGTCAG
2850 TGAAGTGCTT CATGTGGCAG GAGAAAAAG GCTGCACCGG TGCCGTCAGCA
2900 GAATATGTGA TACAGGATAT ATTCCGCTTC CTCGCTCACT GACTCGCTAC
2950 GCTCGGTCGT TCGACTGCGG CGAGCGGAAA TGGCTTACGA ACGGGCGGA
3000 GATTTCCTGG AAGATGCCAG GAAGATACTT AACAGGGAAG TGAGAGGGCC
3050 GCGGCAAAGC CGTTTTTCCA TAGGCTCCGC CCCCCTGACA AGCATCACGA
3100 AATCTGACGC TCAAATCAGT GGTGGCGAAA CCCGACAGGA CTATAAAGAT
3150 ACCAGGCGTT TCCCCTGGCG GCTCCCTCGT GCGCTCTCCT GTTCCTGCCT
3200 TTCGGTTTAC CGGTGTCATT CCGCTGTTAT GGCCGCGTTT GTCTCATTCC
3250 ACGCCTGACA CTCAGTTCCG GGTAGGCAGT TCGCTCCAAG CTGGACTGTA
3300 TGCACGAACC CCCCGTTCAG TCCGACCGCT GCGCCTTATC CGGTAACTAT
3350 CGTCTTGAGT CCAACCCGGA AAGACATGCA AAAGCACCAC TGGCAGCAGC
3400 CACTGGTAAT TGATTTAGAG GAGTTAGTCT TGAAGTCATG CGCCGGTTAA
3450 GGCTAAACTG AAAGGACAAG TTTTGGTGAC TGCGCTCCTC CAAGCCAGTT
3500 ACCTCGGTTC AAAGAGTTGG TAGCTCAGAG AACCTTCGAA AAACCGCCCT
3550 GCAAGGCGGT TTTTTCGTTT TCAGAGCAAG AGATTACGCG CAGACCAAAA
3600 CGATCTCAAG AAGATCATCT TATTAATCAG ATAAAATATT TCTAGATTTC
3650 AGTGCAATTT ATCTCTTCAA ATGTAGCACC TGAAGTCAGC CCCATACGAT
3700 ATAAGTTGTT AATTCTCATG TTTGACAGCT TATCATCGAT
```

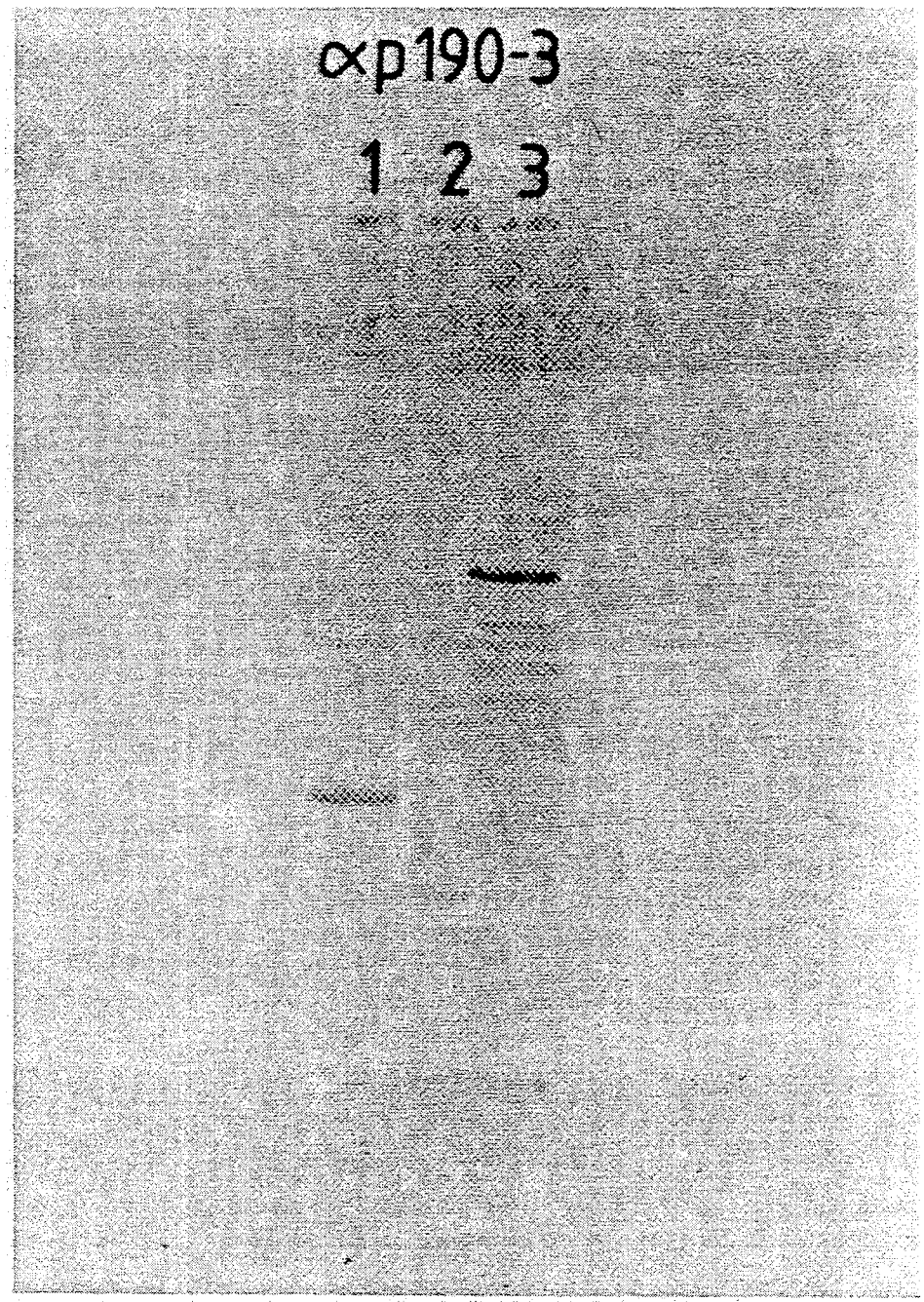
FIG. II

PLASMODIUM FALCIPARUM MEROZOITE ANTIGEN PEPTIDES

TECHNICAL FIELD

This invention relates to *P. falciparum* polypeptide antigens produced by recombinant DNA technology, affinity peptides which may be associated with the antigens, vectors and bacterial transformants, vaccines and antibodies against the peptides.

BACKGROUND OF THE INVENTION

Human malaria is caused by four species of Plasmodium, *P. falciparum*, *P. vivax*, *P. ovale* and *P. malariae*. According to a report of the World Health Organization (WHO) published 1986, there occur every year worldwide nearly a hundred million cases of malaria infection, of which about one million, mostly young children infected with *P. falciparum*, fatal. Due partly to the appearance of drug-resistant parasites and insecticide-resistant mosquito vectors, the incidence of malaria has been increasing. For example, Indian health authorities reported about 100,000 cases of malaria in 1962 and 3 million (mostly due to *P. vivax*) in 1980 (Bruce-Chwatt, Essential Malariology, 2nd edn., Heinemann, London [1985]).

New technical developments have raised hopes that it will become soon possible to produce anti-malaria vaccines which can help to counter the spread of malaria. First, new methods of vaccine development (involving, for example, gene cloning, use of monoclonal antibodies for antigen identification, and immunization with synthetic peptides) can be applied to the case of malaria. Second, long-term cultures of *P. falciparum* in human red blood cells (Trager et al., Science 193, 673-675 [1976]) have provided a ready source of material for the study of the parasite. More recently, it has become possible to maintain all stages of the parasite's life cycle in the laboratory (Ponnudurai et al., Trans. R. Soc. Trop. Med. Hyg. 76, 812-818 [1982]; Mazier et al., Science 227, 440-442 [1985]).

*P. falciparum* spends part of its life-cycle in human red blood cells. A merozoite invades the host cell, enlarges and later undergoes repeated nuclear division to form a schizont. Maturation of the schizont yields a new crop of merozoites which are released into the blood stream and, after a short time, reinvade new erythrocytes.

A protein has been detected on the surface of merozoites and schizonts which could be active as a vaccine against malaria. When synthesized, the protein has an apparent molecular weight of 190,000-200,000 D (Perrin et al., Clin. Exp. Immunol. 41, 91-96 [1980]; Holder et al., J. Exp. Med. 156, 1528-1538 [1982]; Hall et al., Mol. Biochem. Parasitol. 7, 247-265 [1983] and Mol. Biochem. Parasitol. 11, 61-80 [1984]). It has been called GP185, p190, 195-kD protein and polymorphic schizont antigen (PSA). In addition, much, but not all of the protein is lost when merozoites invade new erythrocytes (Holder et al., supra; Hall et al., supra [1983]).

Analogues of p190 are present in all known species of Plasmodium. In all cases tested antibodies against p190 block parasite invasion in vitro (Epstein et al., J. Immunol. 127, 212-217 [1981]; perrin et al., J. Exp. Med. 160, 441-451 [1984]; Boyle et al., Infect. Immun. 38, 94-102 [1982]). Injection of purified p190 protein in Saimiri monkeys leads to at least partial protection against malaria (Hall et al., supra [1984]; Perrin et al., supra [1984]). The gene encoding the p190 protein has been isolated and sequenced from three different parasite isolates, namely the Thai isolate K1 (Mackay et al., EMBO J. 4, 3823-3829 [1985]), the Malaysian isolate CAMP (Weber et al., Nucleic Acids Res. 14, 3311-3323 [1986]) and the West African isolate Wellcome (Holder et al., Nature 317, 270-273 [1985]). Sequence comparisons between these alleles have shown that there is a certain degree of polymorphism between the different isolates. The tripeptide repeats found near the amino-terminus of each allele for example are different in each case studied.

For the development of a vaccine it is necessary to find an epitope on p190 which is present in most or preferably in all isolates, to protect against a wide variety of parasite variants.

SUMMARY OF THE INVENTION

The present invention relates to polypeptides with an amino acid sequence derived from the 190 kD (1 kD=1,000 Daltons) precursor to the major merozoite surface antigens of the K1 isolate of *Plasmodium falciparum*. Said polypeptides are capable of eliciting an immune response against different isolates of *Plasmodium falciparum*. More precisely, the present invention relates to a synthetic polypeptide of the formula $$A—B—C \qquad (I)$$

wherein

A is an affinity peptide residue or may be absent,

B is

ThrLeuCysAspAsnIleHisGlyPheLysTyrLeuIleAspGlyTyrGlu
GluIleAsnGluLeuLeuTyrLysLeuAsnPheTyrPheAspLeuLeuArg
AlaLysLeuAsnAsnValCysAlaAsnAspTyrCysGlnIleProPheAsn
LeuLysIleArgAlaAsnGluLeuAspValLeuLysLysLeuValPheGly
TyrArgLysProLeuAspAsnIleLysAspAsnValGlyLysMetGluAsp
TyrIleLysLysAsnLysLysThrIleGluAsnIleAsnGluLeuIleGlu
GluSerLysLysThrIleAspLysAsnLysAsnAlaThrLysGluGluGlu
LysLysLysLeuTyrGlnAlaGlnTyrAspLeuPheIleTyrAsnLysGln
LeuGluGluAlaHisAsnLeuIleSerValLeuGluLysArgIleAspThr
LeuLysLysAsnGluAsnIleLysGluLeuLeuAspLysIleAsnGluIle
LysAsnProProPro, or a fragment thereof, or AlaGluIleAlaGluThrGluAsnThrLeuGluAsnThrLysIleLeuLeu
LysHisTyrLysGlyLeuValLysTyrTyrAsnGlyGluSerSerProLeu
LysThrLeuSerGluGluSerIleGlnThrGluAspAsnTyrAlaSerLeu
GluAsnPheLysValLeuSerLysLeuGluGlyLysLeuLysAspAsnLeu
AsnLeuGluLysLysLysLeuSerTyrLeuSerArgGlyLeuHisHisLeu
IleAlaGluLeuLysGluValIleLysAsnLysAsnTyrThrGlyAsnSer
ProSerValAsnAsnThrAspValAsnAsnAlaLeuGluSerTyrLysLys
PheLeuProGluGlyThrAspValAlaThrValValSerGluSerGlySer, or a fragment thereof, or a combination of these sequences or fragments, provided that the fragments mentioned above represent or contain at least one epitope of the 190 kD precursor to the major merozoite surface antigens of *P. falciparum* and C is a peptide residue or may be absent.

The invention further relates to immunogenic compositions and vaccines containing a polypeptide as defined above, antibodies raised against said polypeptides, DNA sequences coding for said polypeptides, replicable microbial vectors comprising such DNA sequences and microorganisms transformed with such vectors. Moreover, the invention relates to processes for the production of the above-mentioned polypeptides, immunogenic compositions, microorganisms and antibodies and to the use of said polypeptides or immunogenic compositions for the immunization of mammals against malaria. Furthermore the invention relates to a method of immunizing mammals against malaria.

BRIEF DESCRIPTION OF THE FIGURES

Having now generally described this invention, the same may be more readily understood by reference to the following non-limiting examples in connection with the accompanying drawings, wherein the following abbreviations and symbols are used.

B, E, H, P, S, Sa, Sc, X, Xb which indicate sites for restriction endonucleases BamHI, EcoRI, HindIII, PstI, SphI, SalI, ScaI, XhoI and XbaI, respectively.

represents promoters of the genes bla, lacI and neo;

represents ribosomal binding sites of the genes bla, cat, neo and lacI;

represents terminators $t_o$ and T1;

represents the regulatable promoter/operator element $P_{N25x/O}$;

represents ribosomal binding sites RBSII,SphI and RBSII,3A+5A;

represents coding regions under control of these ribosomal binding sites;

represents regions required for DNA replication (repl.);

represents coding regions for dihydrofolate reductase (dhfr), chloramphenicol acetyltransferase (cat), β-lactamase (bla), lac repressor (lacI) and neomycin phosphotransferase (neo).

Figure 1:
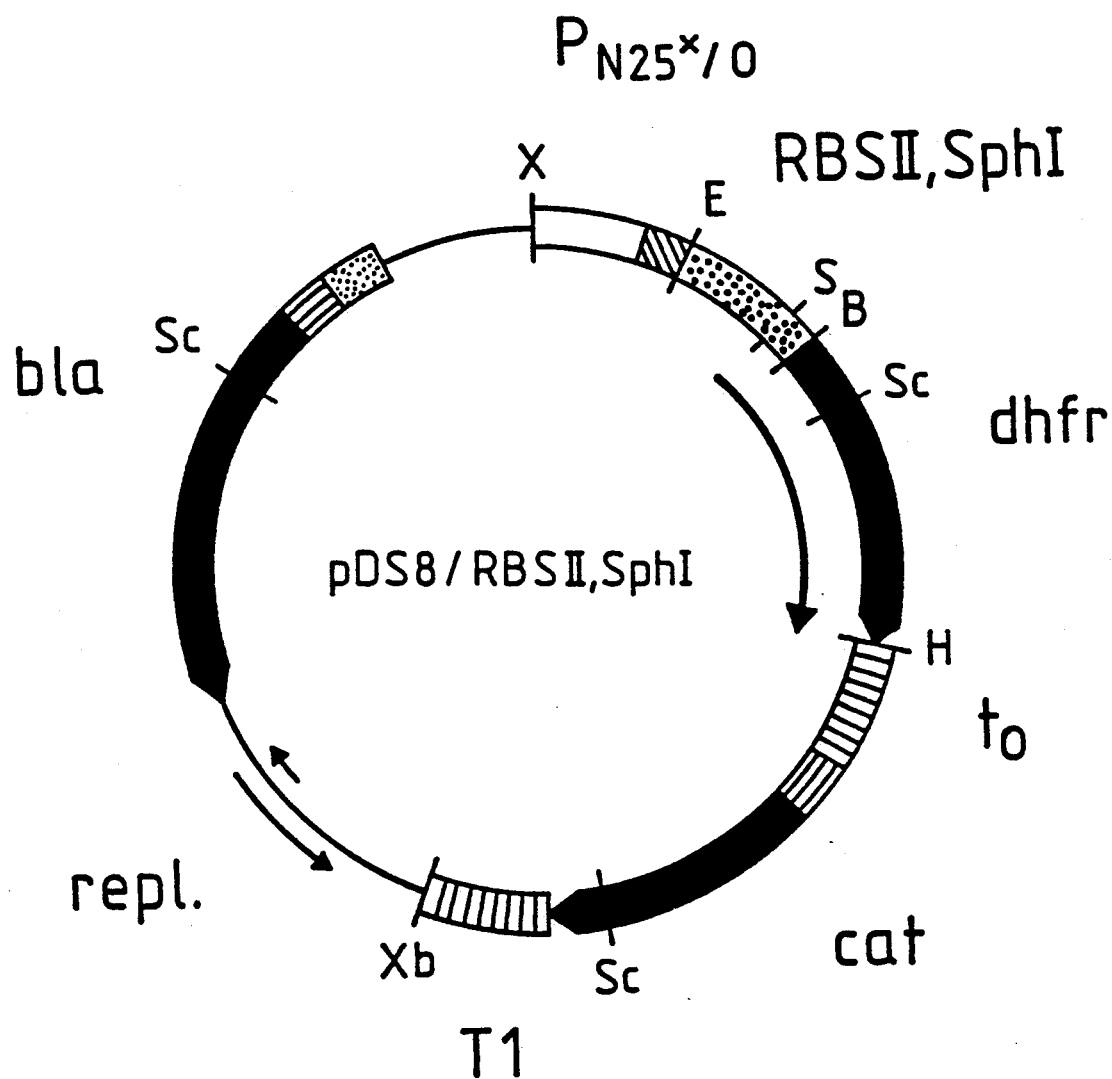
In FIGS. 1, 3 and 5 

FIG. 1:
Schematic drawing of plasmid pDS8/RBSII,SphI.

FIG. 2:
Nucleotide sequence of the XhoI/XbaI fragment of plasmid pDS8/RBSII,SphI containing the regulatable promoter/operator element $P_{N25x/O}$, the ribosomal binding site RBSII,SphI, the dhfr-gene, terminator $t_o$, the cat-gene and terminator T1. The restriction endonuclease sites indicated in FIG. 1 are overlined and the region under control of RBSII,SphI encoding a dihydrofolate reductase polypeptide is underlined. In addition the pBR322 entity of pDS8/RBSII,SphI is schematically shown, where the given numbers refer to the nucleotide sequence of pBR322 (Sutcliffe, Cold Spring Harbor Symp. Quant. Biol. 43, 77–90 [1979]).

Figure 3:
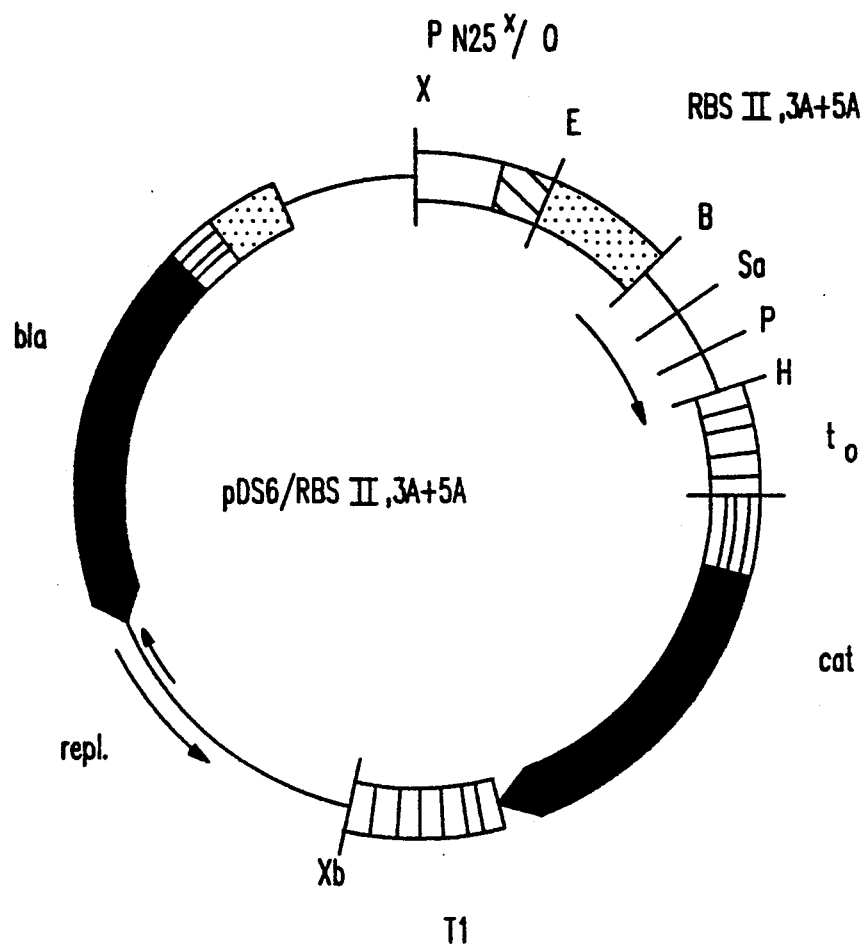

FIG. 3:
Schematic drawing of plasmid pDS6/RBSII,-3A+5A.

FIG. 4:
Nucleotide sequence of the XhoI/XbaI fragment of plasmid pDS6/RBSII,3A.5A containing the regulatable promoter/operator element $P_{N25x/O}$, the ribosomal binding site RBSII,3A+5A, terminator $t_o$, the cat-gene and terminator T1. The restriction endonuclease sites indicated in FIG. 3 are overlined and the region under control of RBSII,3A+5A is underlined. In addition the pBR322 entity of pDS6/RBSII,3A+5A is schematically shown, where the given numbers refer to the nucleotide sequence of pBR322 (Sutcliffe, supra).

Figure 5:
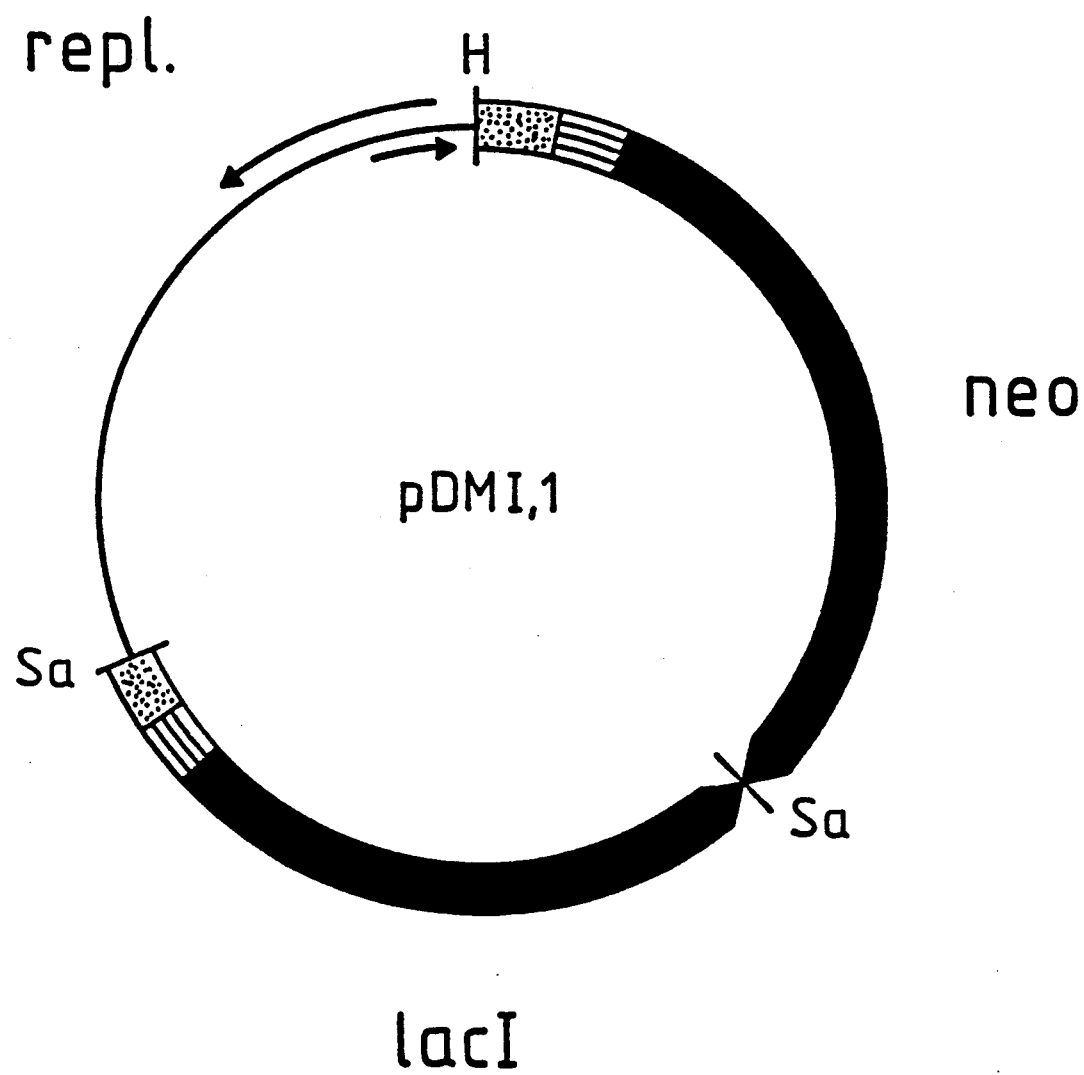

FIG. 5:
Schematic drawing of plasmid pDMI,1.

FIG. 6:
DNA sequence of the pDMI,1. The restriction endonuclease sites indicated in FIG. 5 are overlined and the coding regions for neomycin phosphotransferase (neo) and lac repressor (lacI) are underlined.

Figure 7:
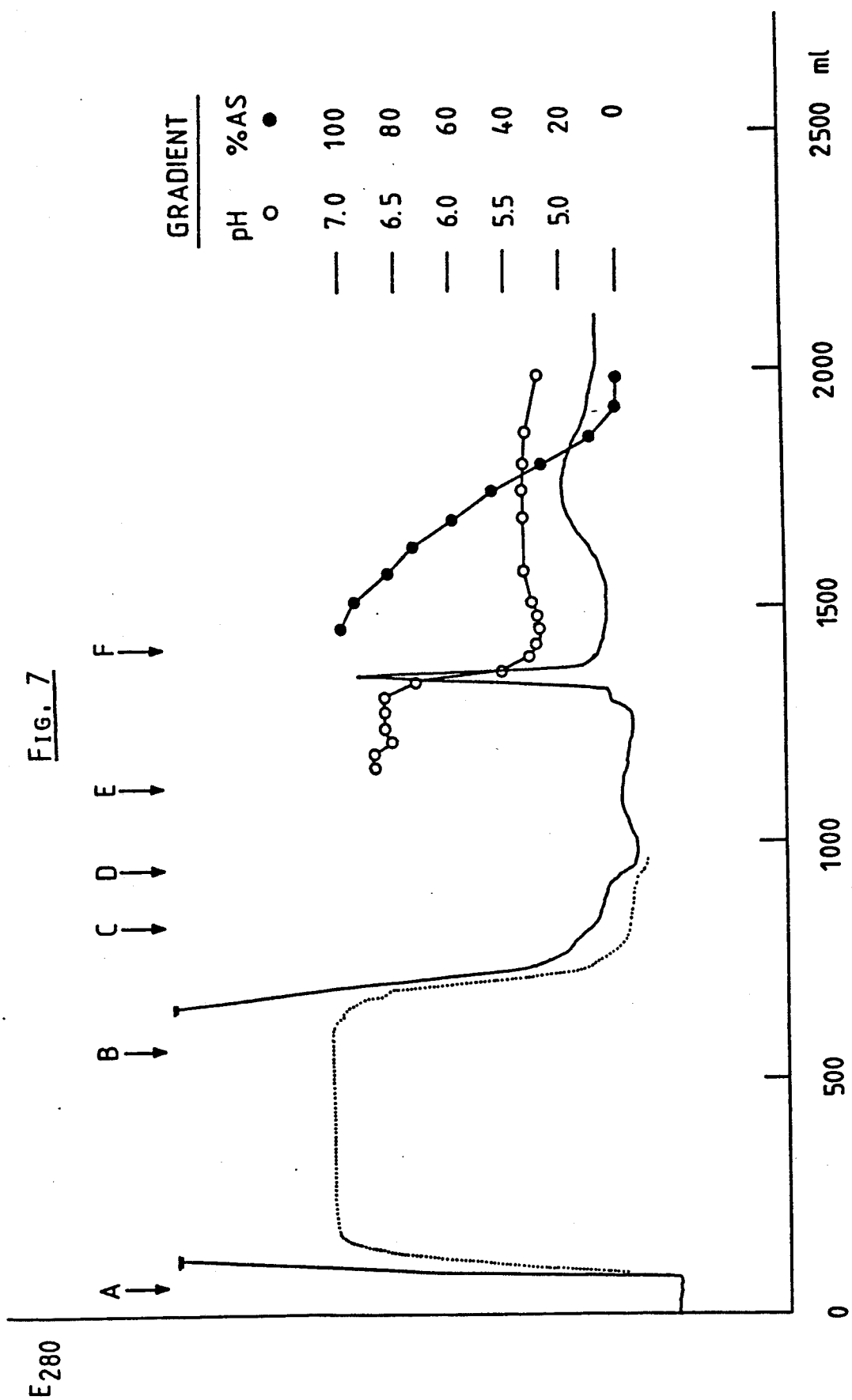

FIG. 7:
Purification of p190-1 on the NTA-nickelchelate column. The trace of the UV-recorder (280 nm) is given as solid or dotted line. The pH-gradient is depicted with open symbols (o) and the $(NH_4)_2SO_4$-gradient with closed symbols (o). Buffer change is indicated by capital letters. A: application of the crude extract. B: wash with 0.1M Tris/HCl (pH 7.5), 0.2M NaCl. C: wash with 0.1M Tris/HCl (pH 6.0), 0.2M NaCl. D: wash with 0.1M Tris/HCl (pH 6.0), 1M $(NH_4)_2SO_4$. E: wash with 0.1M Tris/HCl (pH 4.5), 1M $(NH_4)_2SO_4$. F: gradient elution of p190-1 with 0.1M Tris/HCl (pH 4.5). 0.2M NaCl.

Figure 8:
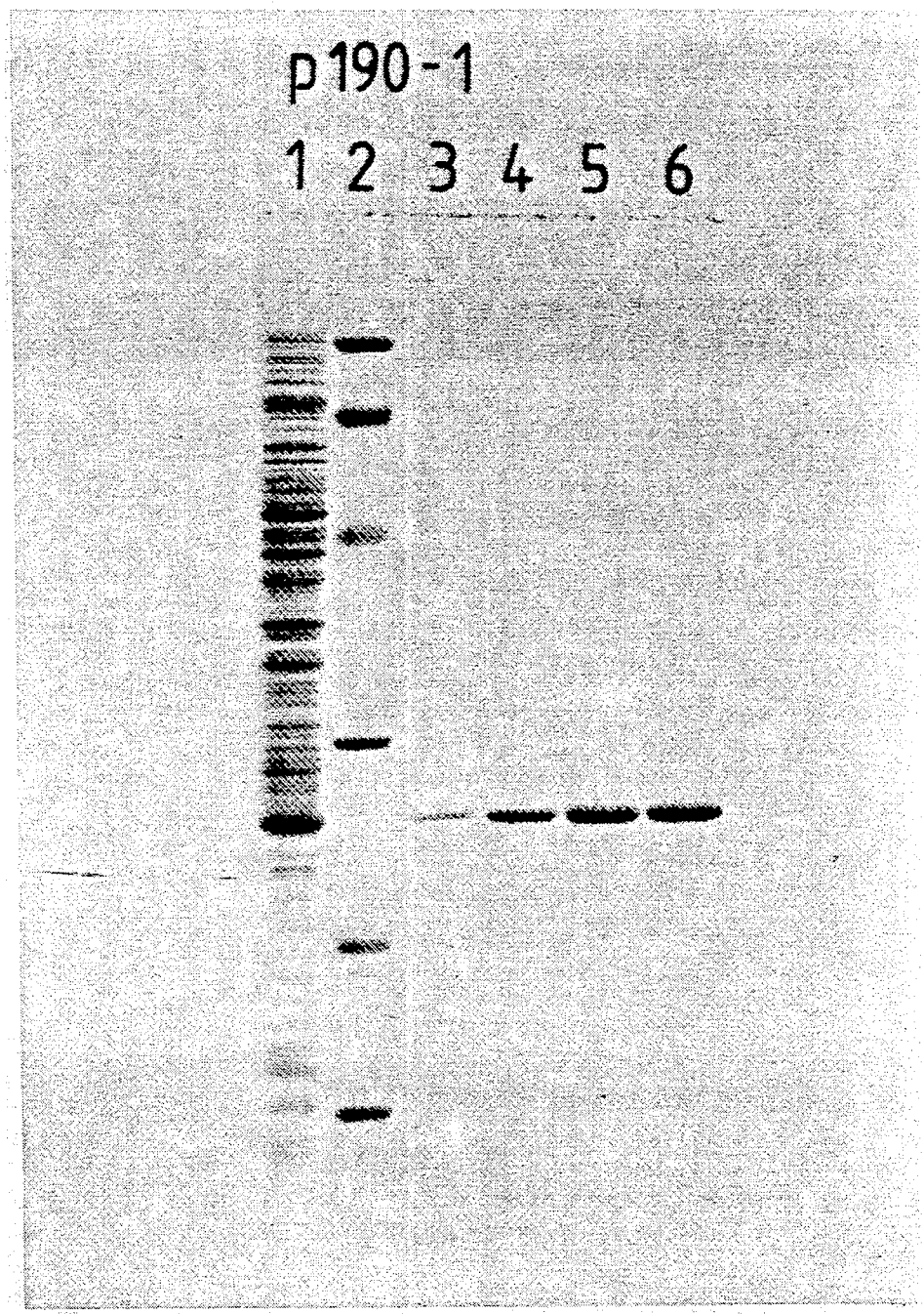

FIG. 8:
Analytical SDS-polyacrylamide gel electrophoresis (SDS-PAGE) of purified p190-1. The polypeptide is in homogeneous form as shown in lanes 3 to 6. Lane 1 shows an E. coli M15 (pGC1,pDMI,1) lysate wherefrom p190-1 has been purified. Lane 2 is a molecular weight marker (Biorad). The electrophoretic mobilities of the marker proteins phosphorylase b [$M_r=92,500$], bovine serum albumin [$M_r=66,200$], ovalbumin [$M_r=45,000$], carbonic anhydrase [$M_r=31,000$], soybean trypsin inhibitor [$M_r=21,500$] and lysozyme [$M_r=14,400$] are indicated by their $M_r$ values ($\times 10^3$). Lanes 3 to 6 contain 0.25, 0.5, 1.0 and 2.0 μg of p190-1 respectively.

Figure 9:
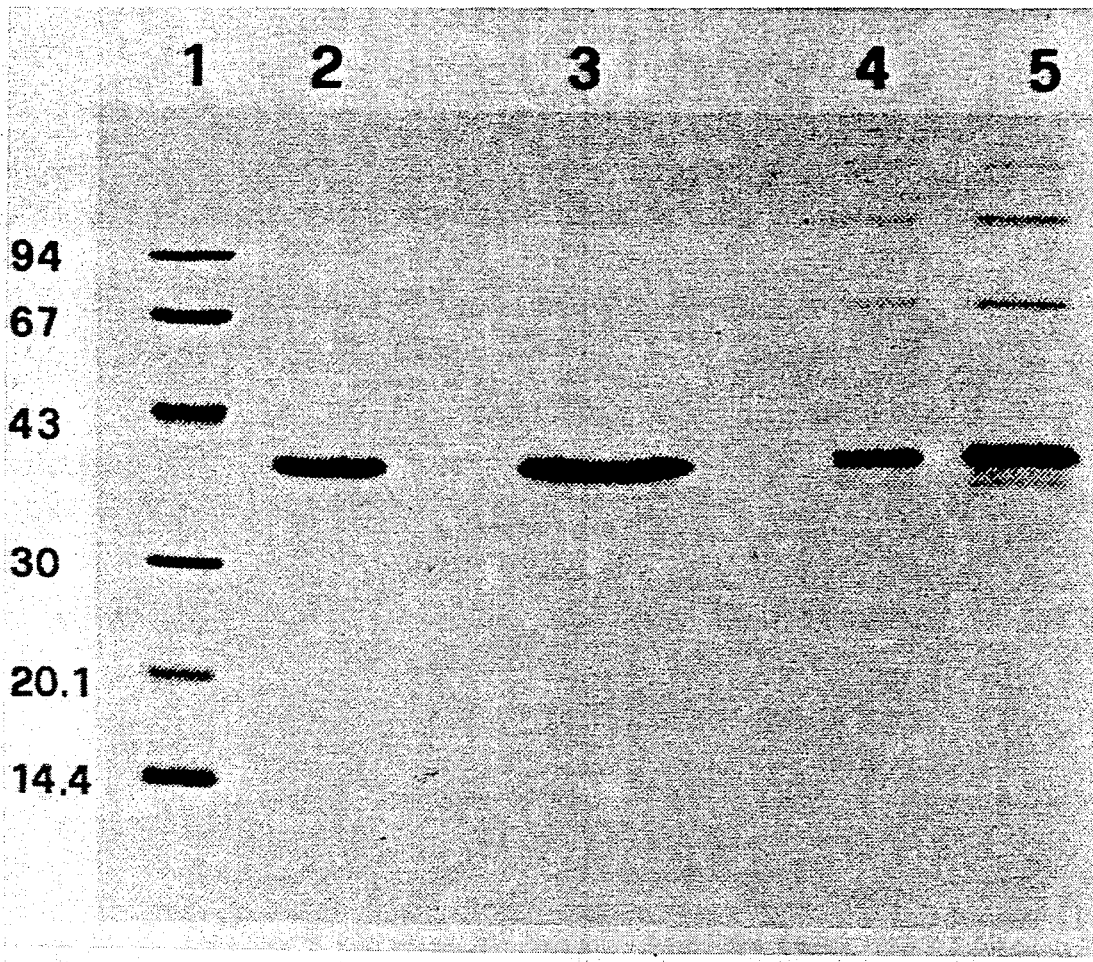

FIG. 9:
Analytical SDS-pAGE of purified p190-3 under reducing (lanes 2 and 3) and non-reducing (lanes 4 and 5) conditions. The polypeptide is in homogeneous form as shown in lanes 2 and 3. Lanes 4 and 5 show that the E. coli lysate contains multimers of the polypeptide which arise by the formation of disulfide bonds between cysteine side groups present in p190-3. Lanes 2 and 4 contain 5 μg and lanes 3 and 5 10 μg protein. Lane 1 is a molecular weight marker (pharmacia). The electrophoretic mobilities of the marker proteins (phosphorylase b [$M_r=94,000$], bovine serum albumin [$M_r=67,000$], ovalbumin [$M_r=43,000$], carbonic anhydrase [$M_r=30,000$], soybean trypsin inhibitor [$M_r=20,100$] and α-lactalbumin [$M_r=14,400$]) are indicated by their $M_r$ values ($\times 10^3$).

Figure 10:
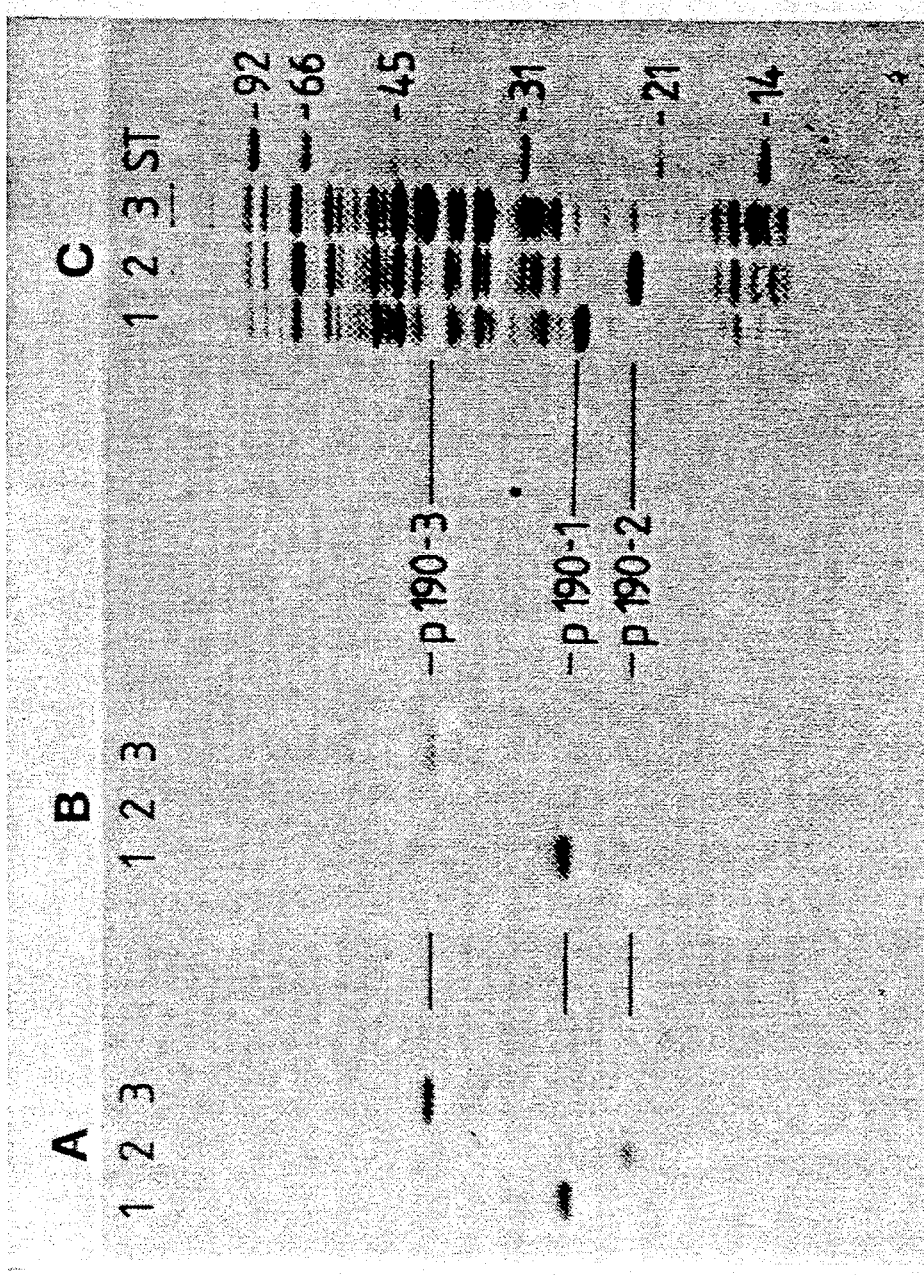

FIG. 10:
Western blot and protein analysis of p190-1, p190-2b and p190-3. Panel A shows a Western-blot of bacterial lysates of E. coli M15(pDMI,1) transformed with pGCI, pGC2b and pGC3 (lanes 1, 2 and 3) which were analyzed using rabbit anti-p190 serum. Panel B shows the same samples analyzed with pooled human sera from endemic areas. The rabbit serum reacts with all three antigens, whereas the human sera react only with bands corresponding in size to the polypeptides p190-1 and p190-3. Antigen-antibody complexes were visualized by using the horseradish peroxidase reaction. Panel C shows a Coomassie blue stained SDS-gel of the same samples. ST indicates a molecular weight standard. Sizes are given in kilo-Daltons molecular weight.

FIG. 11:

Total bacterial lysates of *E. coli* MI5(pDM,1) transformed with pGC1, pGC2b or pGC3 (lanes 1, 2, 3 respectively) were separated in SDS-polyacrylamide gels and transferred to nitrocellulose. The Western-blot was then analyzed using a rabbit serum against p190-3. Antigen/antibody complexes were visualized using the horseradish peroxidase reaction. The rabbit serum against p190-3 reacted as expected with all three antigens.

DESCRIPTION OF THE INVENTION

The polypeptides of the present invention comprise an amino acid sequence derived from the 190 kD precursor to the major merozoite surface antigens of *P. falciparum* which represents at least one epitope which is present in several isolates, e.g., K1, CAMP and the Wellcome isolates.

The polypeptides may contain an affinity peptide residue. Such an affinity peptide residue comprises an amino acid sequence which binds selectively to an affinity chromatography resin. Preferred affinity peptide residues contain two or more adjacent histidine residues. Most preferred affinity peptide residues are MetHisHisAlaProGlySerGly, MetHisHisAlaProGlySer and MetHisHisAlaPro. Polypeptides containing an affinity peptide residue with two or more adjacent histidine residues bind selectively to nitrilotriacetic acid-nickel chelate resins and can therefore be separated from proteins which lack two or more adjacent histidine residues by affinity chromatography.

Preferred polypeptides of the present invention are

MetHisHisAlaProGlySerGlyThrLeuCysAspAsnIleHisGlyPheLysTyrLeu
IleAspGlyTyrGluGluIleAsnGluLeuLeuTyrLysLeuAsnPheTyrPheAspLeu
LeuArgAlaLysLeuAsnAsnValCysAlaAsnAspTyrCysGlnIleProPheAsnLeu
LysIleArgAlaAsnGluLeuAspValLeuLysLysLeuValPheGlyTyrArgLysPro
LeuAspAsnIleLysAspAsnValGlyLysMetGluAspTyrIleLysLysAsnLysLys
ThrIleGluAsnIleAsnGluLeuIleGluGluSerLysLysThrIleAspLysAsnLys
AsnAlaThrLysGluGluGluLysLysLysLeuTyrGlnAlaGlnTyrAspLeuPheIle
TyrAsnLysGlnLeuGluGluAlaHisAsnLeuIleSerValLeuGluLysArgIleAsp
ThrLeuLysLysAsnGluAsnIleLysGluLeuLeuAspLysIleAsnGluIleLysAsn
ProProProAlaGlyGlyLeuLeuLeuIleAspProValMetThrSerGluLeuHisLeu
AspLeuPheArgThrLeuGlyCysArgArgAlaPhePheIleGlyGluAsnProSer
(P190-1);

MetHisHisAlaProGlySerAlaGluIleAlaGluThrGluAsnThrLeuGluAsnThr
LysIleLeuLeuLysHisTyrLysGlyLeuValLysTyrTyrAsnGlyGluSerSerPro
LeuLysThrLeuSerGluGluSerIleGlnThrGluAspAsnTyrAlaSerLeuGluAsn
PheLysValLeuSerLysLeuGluGlyLysLeuLysAspAsnLeuAsnLeuGluLysLys
LysLeuSerTyrLeuSerArgGlyLeuHisHisLeuIleAlaGluLeuLysGluValIle
LysAsnLysAsnTyrThrGlyAsnSerProSerValAsnAsnThrAspValAsnAsnAla
LeuGluSerTyrLysLysPheLeuProGluGlyThrAspValAlaThrValValSerGlu
SerGlySerValAspLeuGlnProSerLeuAspSerCys (p190-2a);

MetHisHisAlaProAlaGluIleAlaGluThrGluAsnThrLeuGluAsnThrLysIle
LeuLeuLysHisTyrLysGlyLeuValLysTyrTyrAsnGlyGluSerSerProLeuLys
ThrLeuSerGluGluSerIleGlnThrGluAspAsnTyrAlaSerLeuGluAsnPheLys
ValLeuSerLysLeuGluGlyLysLeuLysAspAsnLeuAsnLeuGluLysLysLysLeu
SerTyrLeuSerArgGlyLeuHisHisLeuIleAlaGluLeuLysGluValIleLysAsn
LysAsnTyrThrGlyAsnSerProSerValAsnAsnThrAspValAsnAsnAlaLeuGlu
SerTyrLysLysPheLeuproGluGlyThrAspValAlaThrValValSerGluSerGly
SerValAspLeuGlnproSerLeuAspSerCys (p190-2b); and MetHisHisAlaProGlySerAlaGluIleAlaGluThrGluAsnThrLeuGluAsnThr
LysIleLeuLeuLysHisTyrLysGlyLeuValLysTyrTyrAsnGlyGluSerSerPro
LeuLysThrLeuSerGluGluSerIleGlnThrGluAspAsnTyrAlaSerLeuGluAsn
PheLysValLeuSerLysLeuGluGlyLysLeuLysAspAsnLeuAsnLeuGluLysLys
LysLeuSerTyrLeuSerArgGlyLeuHisHisLeuIleAlaGluLeuLysGluValIle
LysAsnLysAsnTyrThrGlyAsnSerProSerValAsnAsnThrAspValAsnAsnAla
LeuGluSerTyrLysLysPheLeuProGluGlyThrAspValAlaThrValValSerGlu
SerGlySerGlyThrLeuCysAspAsnIleHisGlyPheLysTyrLeuIleAspGlyTyr
GluGluIleAsnGluLeuLeuTyrLysLeuAsnPheTyrPheAspLeuLeuArgAlaLys
LeuAsnAsnValCysAlaAsnAspTyrCysGlnIleProPheAsnLeuLysIleArgAla
AsnGluLeuAspValLeuLysLysLeuValPheGlyTyrArgLysProLeuAspAsnIle
LysAspAsnValGlyLysMetGluAspTyrIleLysLysAsnLysLysThrIleGluAsn
IleAsnGluLeuIleGluGluSerLysLysThrIleAspLysAsnLysAsnAlaThrLys
GluGluGluLysLysLysLeuTyrGlnAlaGlnTyrAspLeuPheIleTyrAsnLysGln
LeuGluGluAlaHisAsnLeuIleSerValLeuGluLysArgIleAspThrLeuLysLys
AsnGluAsnIleLysGluLeuLeuAspLysIleAsnGluIleLysAsnProProProAla
GlyGlyLeuLeuLeuIleAspProValMetThrSerGluLeuHisLeuAspLeuPheArg
ThrLeuGlyCysArgArgAlaPhePheIleGlyGluAsnProSer (P190-3).

The invention also relates to homologs of these polypeptides and to polypeptides derived from the above mentioned polypeptides by amino acid substitution(s), provided these polypeptides are still capable of eliciting an immune response in a host against different isolates of *P. falciparum* or at least against the K1. CAMP, MAD-20 and Wellcome isolates of *P. falciparum*. Said polypeptides can be used for the immunization of mammals against malaria.

Amino acid substitutions in polypeptides which do not essentially alter the biological activities of the polypeptide in question are known in the art. Such amino acid substitutions are described e.g. by Doolittle in "The Proteins", Neurath, H. and Hill, R. L., Eds., Academic Press, New York [1979]. The most frequently observed amino acid substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu and vice versa.

In the general formula A-B-C mentioned above, only subsequence B corresponds to part of the 190 kD protein of P. falciparum. A and C may either be absent or represent the amino acid sequences defined above. Furthermore, they may be composed of any amino acid sequence which is not detrimental to the use of the polypeptides as a vaccine for the immunization of mammals against malaria. Thus, A can be a partial sequence or an extension of amino acid sequence MetHisHisAlaProGlySerGly, as long as that sequence contains at least two adjacent histidine residues. This sequence A represents an affinity peptide which may be used as a vehicle to purify the polypeptides of the invention by using the resin and method described in Example 2, F and G, respectively.

Likewise, in addition to the preferred sequences representing C, which are AlaGlyGlyLeuLeuLeuIleAspProValMetThrSerGlu LeuHisLeuAspLeuPheArgThrLeuGlyCysArgArgAlaPhePheIleGlyGluAsnProSer or ValAspLeuGlnProSerLeuAspSerCys, this residue may be composed of any amino acid sequence which does not interfere with the use of the polypeptides of the invention. The specific sequences of C defined above are derived from the expression vector in which the P. falciparum specific sequence B has been cloned. A and C are, therefore, present for technical reasons only and can vary within wide limits comprehensible to the man skilled in the art.

The polypeptides of the present invention may be adsorbed or covalently attached to a carrier material. Suitable carrier materials are natural or synthetic polymeric compounds, such as copolymers of one or more amino acids (e.g., polylysine) or sugars (e.g., polysaccharides). Further suitable carrier materials are natural or synthetic polypeptides such as hemocyanins [e.g., KLH (keyhole limpet hemocyanin)], serum proteins (e.g., gammaglobulins, serum albumins) and toxoids (e.g., diptheria toxoid and tetanus toxoid). Other suitable carrier materials known in the art will be suggested by these examples.

The covalent coupling of the polypeptides of the invention to the carrier material can be carried out in a manner well known in the art, e.g., directly by the formation of peptide or ester bonds between free carboxyl, amino or hydroxyl groups in the polypeptides and corresponding groups on the carrier material or, alternatively, by bonding through a conventional bifunctional linking group. Thus, for example, for direct covalent coupling, it is possible to utilize a carbodiimide, most preferably 1,3-dicyclohexyl carbodiimide or 1-ethyl-3-(3-dimethylaminopropyl) carbodiimide, a $C_{2-7}$ dialkanal such as glutaraldehyde (Avrameas, Immunochem. 6, 43–52 [1969]) or m-maleimidobenzoyl-N-hydroxysuccinimide (MBS).

The carrier material with the bound polypeptides can be purified from unbound polypeptides and if necessary from excess coupling reagents by methods well known in the art (e.g. dialysis or column chromatography).

The peptides of this invention can be prepared by conventional peptide synthetic methods, either in solution or, preferably, in solid phase, such as the method of Merrifield (J. Am. Chem. Soc. 85, 2149-2154 [1963]) or other equivalent methods known in the art.

Solid phase synthesis is commenced from the C-terminal end of the peptide by coupling a protected amino acid to a suitable resin. A starting material can be prepared by attaching an amino-protected amino acid via a benzyl ester linkage to a chloromethylated resin or a hydroxymethyl resin or via an amide bond to a benzhydrylamine (BHA) resin or methylbenzhydrylamine (MBHA) resin. These resins are available commercially, and their preparation and use are well known.

General methods for protecting and removing protecting groups from amino acids which can be used in this invention are described in "The Peptides", Vol. 2 (E. Gross and J. Meienhofer, Eds., Academic press, New York, pp. 1–284 [1979]). Protecting groups include e.g., the tert-butyloxycarbonyl (Boc), benzyl (Bzl), 2-chlorobenzyloxycarbonyl (2Cl-Z), dichlorobenzyl (Dcb) and 3,4-dimethylbenzyl (Dmb) groups.

After removal of the α-amino protecting group from the initial (C-terminal) amino acid, the remaining protected amino acids are coupled step-wise in the desired order. The entire peptide may be synthesized in this way. Alternatively, small polypeptides may be constructed which are later joined, to give the final peptide product. Appropriate coupling reagents are known in the art, with dicyclohexylcarbodiimide (DCC) being particularly suitable.

Each protected amino acid or peptide is introduced into the solid phase reactor in excess, and the coupling may be carried out in a medium of dimethylformamide (DMF) or methylene chloride ($CH_2Cl_2$), or mixtures thereof. In cases where incomplete coupling occurs, the coupling procedure is repeated before removal of the Nα-amino protecting group prior to the coupling of the next amino acid. The success of the coupling reaction at each stage of synthesis may be monitored. A preferred method of monitoring the synthesis is by the ninhydrin reaction. The coupling reactions and washing steps can be performed using automated instrumentation.

Cleavage of the peptide from the resin can be effected using procedures well known in peptide chemistry. For example, reaction with hydrogen fluoride in the presence of p-cresol and dimethylsulfide at 0° C. for 1 hour may be followed by a second reaction with hydrogen fluoride in the presence of p-cresol for 2 hours at 0° C. Cleavage of peptides from chloromethylated or hydroxymethyl resin supports produces finished peptides having carboxyl groups at the C-termini. Cleavage of peptides from benzhydrylamine or methylbenzhydrylamine resins produces peptides having C-terminal amide groups.

Finally, alternatively and preferably the polypeptides of the present invention can be prepared using methods of the recombinant DNA technology, e.g., as described by Maniatis et al. in "Molecular Cloning—A Laboratory Manual", Cold Spring Harbor Laboratory [1982]. In one such procedure a DNA fragment coding for a polypeptide of the invention may be chemically synthesized by conventional methods, e.g., by the phosphotriester method which is described by Narang et al., Meth. Enzymol. 68, 90–108 [1979], or by the phosphodiester method as described by Brown et al., Meth. Enzymol. 68, 109–151 [1979]. In both methods oligonucleotides are prepared which can then be joined together in a predetermined way to form the desired DNA fragment. The nucleotide sequence of said DNA fragment may be identical to one found in the DNA of an isolate of P. falciparum or may be different. The degeneracy of the genetic code permits substantial freedom in the choice of codons for any given amino acid sequence so that different DNA fragments coding for the same compound can be constructed. The codons selected can be adapted to the preferred codon usage of the host used to express the recombinant polypeptide (Grosjean et al., Gene 18, 199-209 (1982)). Care has to be taken that no nucleotide sequence is selected which makes the construction of the expression vector for said polypeptide difficult. e.g., by introducing an undesired restriction site, or which is detrimental to the expression of said polypeptide.

In another procedure used in recombinant DNA technology the DNA fragment coding for a polypeptide of the invention can be isolated from genomic DNA of an isolate of *P. falciparum*. This can be done by partially digesting said genomic DNA with a suitable restriction endonuclease, e.g., with EcoRI, isolating fragments with a length ranging from 1.5 to 8 × 10³ base pairs after separation of the digested DNA on a 0.7% Agarose gel and cloning said fragments into a suitable vector, e.g., the lambda vector gt11 (ATCC No. 37194, also available as protoclone GT TM lambda GT11, Genofit SA, Geneva) according to the instructions given by the manufacturer. The recombinant phage DNA can then be packaged in vitro (Gigapack TM, Vector Cloning Systems, San Diego) and the resulting phages can be transfected in a suitable host, e.g., in *E. coli* Y1088 (ATCC No. 37195). About 100,000 recombinant phages are then screened for the presence of *P. falciparum* specific DNA by hybridization with radioactive labelled complementary oligonucleotide probes. These probes can be based on partial sequences from the known nucleotide sequences of the different isolates of *P. falciparum*. Complementary oligonucleotide probes may be chemically synthesized as described above. Examples for such oligonucleotide probes are the oligonucleotide 1 (35-mer) having the sequence

TTTTATTTTGATTTATTAAGAGCAAAAT-
TAAATAA and the oligonucleotide 2 (33-mer) having the sequence

GAAAACACAAAAATATTATTGAAACAT-
TATAAA which are derived from the nucleotide sequence of the K1 isolate of *P. falciparum* (Mackay et al., supra).

Recombinant phages selectively hybridizing with a given oligonucleotide probe can be isolated. The phages can be grown up and the DNA can be isolated. The *P. falciparum* insert can be released and subcloned into a suitable vector. e.g., plasmid pUC19 (pharmacia). The resulting recombinant plasmid can again be subcloned to yield the DNA fragment coding for part B of the polypeptide of the invention.

In one such subcloning procedure, the DNA fragment obtained according to one of the two procedures described above is inserted into a replicable microbial vector. The present invention relates also to such replicable microbial vectors comprising a DNA fragment described above. Such vectors may be used, e.g., as DNA probes in diagnostic tests. The gene probe technology has been reviewed by Klausner et al. in Bio/-Technology, August 1983, pp. 471-478. The application of this technology to prepare DNA probes based on the DNA fragments mentioned above is within the skills of an artisan in the field, as is the selection of a suitable vector for use as a cloning vehicle in the present invention.

For the production of the polypeptides of the present invention in a host, the DNA fragment with a nucleotide sequence derived from one of the isolates of *P. falciparum* has to contain a start codon (i.e., ATG) and a termination codon (TAA, TAG or TGA). If these signals are not present in the original DNA fragment they may be added to the above DNA fragment by methods known in the art. In one such method the DNA fragment is inserted into a vector comprising these signals in such a wa that the start codon and the termination codon are in frame with the sequence coding for subsequence B of the polypeptide of the invention. One or more nucleotide triplets may be present between the start codon and the sequence coding for subsequence B. These nucleotides together with the startcodon code then for sub-sequence A of the polypeptide of the invention. Similarly one or more nucleotide tripletts may be present between the sequence coding for subsequence B and the termination codon. These nucleotides code then for subsequence C of the polypeptide of the invention. Thus, a DNA sequence coding for a polypeptide of the present invention can be obtained using methods well known in the art. The present invention relates also to such DNA sequences.

Preferred DNA sequences coding for polypeptides p190-1, p190-2a, p190-2b or p190-3 respectively, are:

```
ATG CAT CAC GCC CCC GGA TCC GGA ACT TTG TGT GAT AAT ATT CAT
GGT TTC AAA TAT TTA ATT GAT GGA TAT GAA GAA ATT AAT GAA TTA
TTA TAT AAA TTA AAC TTT TAT TTT GAT TTA TTA AGA GCA AAA TTA
AAT AAT GTA TGT GCT AAT GAT TAT TGT CAA ATA CCT TTC AAT CTT
AAA ATT CGT GCA AAT GAA TTA GAC GTA CTT AAA AAA CTT GTG TTC
GGA TAT AGA AAA CCA TTA GAC AAT ATT AAA GAT AAT GTA GGA AAA
ATG GAA GAT TAC ATT AAA AAA AAT AAA AAA ACC ATA GAA AAT ATA
AAT GAA TTA ATT GAA GAA AGT AAG AAA ACA ATT GAT AAA AAT AAG
AAT GCA ACT AAA GAA GAA GAA AAA AAA AAA TTA TAC CAA GCT CAA
TAT GAT CTT TTT ATT TAC AAT AAA CAA TTA GAA GAA GCA CAT AAT
TTA ATA AGC GTT TTA GAA AAA CGT ATT GAC ACT TTA AAA AAA AAT
GAA AAC ATT AAG GAA TTA CTT GAT AAG ATA AAT GAA ATT AAA AAT
CCC CCA CCG GCC GGT GGA CTC CTG TTG ATA GAT CCA GTA ATG ACC
TCA GAA CTC CAT CTG GAT TTG TTC AGA ACG CTC GGT TGC CGC CGG
GCG TTT TTT ATT GGT GAG AAT CCA AGC TAG;

ATG CAT CAC GCC CCC GGA TCC GCT GAA ATA GCA GAA ACT GAA AAC
ACA TTA GAA AAC ACA AAA ATA TTA TTG AAA CAT TAT AAA GGA CTT
GTT AAA TAT TAT AAT GGT GAA TCA TCT CCA TTA AAA ACT TTA AGT
GAA GAA TCA ATT CAA ACA GAA GAT AAT TAT GCC AGT TTA GAA AAC
TTT AAA GTA TTA AGT AAA TTA GAA GGA AAA TTA AAG GAT AAT TTA
AAT TTA GAA AAG AAA AAA TTA TCA TAC TTA TCA AGA GGT TTA CAT
CAT TTA ATT GCT GAA TTA AAA GAA GTA ATA AAA AAT AAA AAT TAT
```

-continued

```
ACA GGT AAT TCT CCA AGC GTA AAT AAT ACG GAT GTT AAC AAT GCA
TTA GAA TCT TAC AAA AAA TTT CTC CCA GAA GGA ACA GAT GTT GCA
ACA GTT GTA AGT GAA AGT GGA TCC GTC GAC CTG CAG CCA AGC TTG
GAC TCC TGT TGA;

ATG CAT CAC GCC CCC GCT GAA ATA GCA GAA ACT GAA AAC ACA TTA
GAA AAC ACA AAA ATA TTA TTG AAA CAT TAT AAA GGA CTT GTT AAA
TAT TAT AAT GGT GAA TCA TCT CCA TTA AAA ACT TTA AGT GAA GAA
TCA ATT CAA ACA GAA GAT AAT TAT GCC AGT TTA GAA AAC TTT AAA
GTA TTA AGT AAA TTA GAA GGA AAA TTA AAG GAT AAT TTA AAT TTA
GAA AAG AAA AAA TTA TCA TAC TTA TCA AGA GGT TTA CAT CAT TTA
ATT GCT GAA TTA AAA GAA GTA ATA AAA AAT AAA AAT TAT ACA GGT
AAT TCT CCA AGC GTA AAT AAT ACG GAT GTT AAC AAT GCA TTA GAA
TCT TAC AAA AAA TTT CTC CCA GAA GGA ACA GAT GTT GCA ACA GTT
GTA AGT GAA AGT GGA TCC GTC GAC CTG CAG CCA AGC TTG GAC TCC
TGT TGA; and ATG CAT CAC GCC CCC GGA TCC GCT GAA ATA GCA GAA ACT GAA AAC
ACA TTA GAA AAC ACA AAA ATA TTA TTG AAA CAT TAT AAA GGA CTT
GTT AAA TAT TAT AAT GGT GAA TCA TCT CCA TTA AAA ACT TTA AGT
GAA GAA TCA ATT CAA ACA GAA GAT AAT TAT GCC AGT TTA GAA AAC
TTT AAA GTA TTA AGT AAA TTA GAA GGA AAA TTA AAG GAT AAT TTA
AAT TTA GAA AAG AAA AAA TTA TCA TAC TTA TCA AGA GGT TTA CAT
CAT TTA ATT GCT GAA TTA AAA GAA GTA ATA AAA AAT AAA AAT TAT
ACA GGT AAT TCT CCA AGC GTA AAT AAT ACG GAT GTT AAC AAT GCA
TTA GAA TCT TAC AAA AAA TTT CTC CCA GAA GGA ACA GAT GTT GCA
ACA GTT GTA AGT GAA AGT GGA TCC GGA ACT TTG TGT GAT AAT ATT
CAT GGT TTC AAA TAT TTA ATT GAT GGA TAT GAA GAA ATT AAT GAA TTA TTA TAT AAA TTA AAC TTT TAT TTT GAT TTA TTA AGA GCA AAA
TTA AAT AAT GTA TGT GCT AAT GAT TAT TGT CAA ATA CCT TTC AAT
CTT AAA ATT CGT GCA AAT GAA TTA GAC GTA CTT AAA AAA CTT GTG
TTC GGA TAT AGA AAA CCA TTA GAC AAT ATT AAA GAT AAT GTA GGA
AAA ATG GAA GAT TAC ATT AAA AAA AAT AAA AAA ACC ATA GAA AAT
ATA AAT GAA TTA ATT GAA GAA AGT AAG AAA ACA ATT GAT AAA AAT
AAG AAT GCA ACT AAA GAA GAA GAA AAA AAA AAA TTA TAC CAA GCT
CAA TAT GAT CTT TTT ATT TAC AAT AAA CAA TTA GAA GAA GCA CAT
AAT TTA ATA AGC GTT TTA GAA AAA CGT ATT GAC ACT TTA AAA AAA
AAT GAA AAC ATT AAG GAA TTA CTT GAT AAG ATA AAT GAA ATT AAA
AAT CCC CCA CCG GCC GGT GGA CTC CTG TTG ATA GAT CCA GTA ATG
ACC TCA GAA CTC CAT CTG GAT TTG TTC AGA ACG CTC GGT TGC CGC
CGG GCG TTT TTT ATT GGT GAG AAT CCA AGC TAG.
```

To express a polypeptide in a host, the DNA sequence coding for said polypeptide has to be operably linked to an expression control sequence. Suitable expression control sequences are well-known in the art and described in various publications, such as European patent Application, publication No. 186 069, published Jul. 2, 1986. The skilled art worker may easily select from these expression control sequences those that are most effective for expressing the polypeptides of the present invention without undue experimentation and without departing from the scope of this invention. The preferred expression control sequence is the one contained in pDS6/RBSII,SphI-His,His. This expression vector is derived from the expression vectors pDS6/RBSII,3A.5A and pDS8/RBSII,SphI. The expression vector pDS6/RBSII,3A+5A was deposited on Oct. 3, 1985 at the Deutsche Sammlung von Mikroorganismen (DSM) in the form of a sample of E. coli M15(pDS6/RBSII,3A+5A;pDMI,1) and assigned accession number DSM 3518. The expression vector pDS8/RBSII,SphI Was deposited on August 6, 1986 at the Deutsche Sammlung von Mikroorganismen (DSM) in the form of a sample of E. coli M15(pDS8/RBSII,SphI;pDMI,1) and assigned accession number DSM 3809. Both deposits were done in accordance with the Budapest Treaty. The construction of the expression vector pDS6/RBSII,SphI-His,His is explained in Example 1. Upon insertion of the DNA fragment with a nucleotide sequence derived from one of the isolates of P. falciparum into said expression vector, a new replicable microbial vector is obtained, which is capable of expressing a polypeptide of the present invention. The construction of such vectors are described in Examples 2, 3 and 4. The resulting vectors pGC1, pGC2a, pGC2b and pGC3 are the preferred vectors of the present invention.

The expression vector containing a DNA sequence coding for a polypeptide of the invention may be inserted into a suitable host organism capable of expressing said polypeptide, using methods well known in the art. The transformants obtained in this way are cultured under conditions permitting the production of large amounts of polypeptide. The recombinant polypeptides may then be isolated and purified by methods known in the art. The present invention relates also to such transformants.

The selection of a particular host for use in this invention is dependent upon a number of factors recognized by the art. These include, for example, compatibility with the chosen expression vector, toxicity of the encoded recombinant polypeptide to the host, ease of recovery of the desired polypeptide, expression characteristics, biosafety and costs. Within these general guidelines, examples of useful bacterial hosts are gram-negative and gram-positive bacteria, especially strains of E. coli and B. subtilis. The most preferred host cell of this invention is E. coli M15 (described as DZ291 in M. R. Villarejo et al., J. Bacteriol., 120, 466–474 [1974]). However, other E. coli strains, such as E. coli 294 (ATCC No. 31446), E. coli RR1 (ATCC No. 31343) and E. coli W3110 (ATCC No. 27325), can also be used.

Once the transformant capable of carrying out the expression of the polypeptides of the present invention has been prepared, the process of the invention can be carried out in a variety of ways, depending upon the nature of the construction of the expression vectors and upon the growth characteristics of the host. Typically, the transformant will be grown under conditions which are favorable for the production of large quantities of cells. When a large number of cells has accumulated, suitable inducers or derepressors in the growth medium or a temperature-shift cause the control sequence supplied with such DNA sequence to become active, permitting the transcription and translation of the coding sequence. In the present invention the expression of the DNA fragment encoding the polypeptide of the present invention is inhibited by the lac repressor. When a large number of cells has accumulated, the control sequence is derepressed by the addition of isopropyl-$\beta$-D-thiogalactopyranoside (IPTG). The polypeptide produced by the recombinant cell can be released by lysing the cell by conventional means well known in the art. The particular means of lysing will depend upon the host cell utilized. When a suitable host is used, the polypeptide of the present invention may also be secreted directly into the medium by the transformant.

When the polypeptides of the present invention are produced in a microbial host the methionine residue at the N-terminus derives from the mRNA translational start signal AUG (encoded on the DNA by the start codon ATG) which codes for the amino acid methionine. In certain expression systems this methionine residue is processed away. The presence or absence of the N-terminal methionine has been found not to impair the biological activity of most recombinant polypeptides (Winnacker, in "Gene und Klone" p. 255, Verlag Chemie (VCH), Weinheim [1985]).

The polypeptides of the present invention can be purified by known methods, such as differential centrifugation, precipitation with ammonium sulfate, dialysis to remove salts (under normal or reduced pressure), preparative isoelectric focusing, preparative gel electrophoresis or various chromatographical methods, e.g., gel filtration, high performance liquid chromatography (HPLC), ion exchange chromatography, reverse phase chromatography and affinity chromatography (e.g., on Blue pharose TM CL-6B, on monoclonal antibodies against said polypeptide coupled to a carrier material, or on metal chelate resins as they are described in the present invention.

A preferred method for the purification of the polypeptides of the invention is the purification by affinity chromatography on metal chelate resins (Sulkowski, Trends in Biotech, 3, 1-7 [1985]). One method uses the selective binding of adjacent histidine residues present in the polypeptides of the present invention to nitrilotriacetic acid-nickelchelate resins. These metal chelate resins contain nitrilotriacetic acid (NTA) derivatives, especially the nitrilotriacetic acid derivative N-[3-amino-1-carboxypropyl]iminodiacetic acid and the N-[5-amino-1-carboxypentyl]iminodiacetic acid, which are covalently bound via a spacer to a matrix. Preferred spacer molecules are those generally used in the preparation of affinity chromatography resins such as the radicals —O—CH$_2$—CH(OH)—CH$_2$— or —O—CO—. Preferred matrices are crosslinked dextrans, agarose (like Sepharose TM) or polyacrylamides. The method for the preparation of the NTA-resin of the formula [Sepharose TM CL-6B]—O—CH$_2$—CH(OH)—CH$_2$—NH(CH$_2$)$_4$—CH(COOH) —N(CH$_2$COO—)-$_2$Ni$^{2+}$ is described in Example 2, F.

The polypeptides of the present invention may form multimers, e.g., dimers, trimers or tetramers or may be part of a fusion polypeptide. Multimers may arise, e.g., upon production of the polypeptide in a microbial host by the formation of disulfide bonds between cysteine side groups (see for example FIG. 9). A fusion polypeptide may be obtained by linking a DNA sequence coding for a polypeptide of the present invention with a DNA sequence selected from a large variety of DNA sequences that encode procaryotic or eucaryotic polypeptides. After expression of the fusion polypeptide encoded by the combined DNA sequences in a suitable host, the fusion polypeptide may be purified by affinity chromatography using a ligand specific for said procaryotic or eucaryotic polypeptide.

An example of such a fusion polypeptide is a fusion polypeptide comprising a polypeptide of the present invention and a polypeptide of active $\beta$-galactosidase. Such fusion proteins can be prepared and purified as described by Rüther et al., EMBO J., 2, 1791-1794 [1983].

A further example of a fusion polypeptide is a fusion polypeptide comprising two or more polypeptides of the present invention. An example of such a polypeptide is p190-3. The amino acid sequence of this polypeptide comprises the sub-sequences B within the amino acid sequence of the polypeptides p190-1 and p190-2a, respectively. It is within the scope of the invention to couple the amino acid sequences making part of the fusion polypeptide directly via a peptide or other bond or via a peptide fragment comprising one, two or more amino acids. Such a peptide fragment may be introduced for technical reasons during the construction of the expression vector encoding the fusion polypeptide.

The present invention relates also to immunogenic compositions containing a polypeptide of the present invention and a pharmaceutically acceptable adjuvant. Said immunogenic compositions are capable of eliciting formation of antibodies specific for the p190 precursor to the major merozoite surface antigens of P. falciparum in a host. Since these antigens are immunologically reactive determinants on the malaria parasite the polypeptides and the immunogenic compositions described above can be used as a vaccine in mammals for providing protective immunity against malaria. The term "pharmaceutically acceptable adjuvant" can mean either the standard compositions which are suitable for human administration or the typical adjuvants employed in animal vaccinations.

Suitable adjuvants for the vaccination of animals include but are not limited to Freund's complete or incomplete adjuvant (not suitable for human or livestock use), Adjuvant 65 (containing peanut oil, mannide monooleate and aluminum monostearate), mineral gels such as aluminum hydroxide, aluminum phosphate and alum, surfactants such as hexadecylamine, octadecylamine, lysolecithin, dimethyldioctadecylammonium bromide, N,N-dioctadecyl-N',N'-bis(2-hydroxyethyl)-propanediamine, methoxyhexadecylglycerol and pluronic polyols, polyanions such as pyran, dextran sulfate, polyIC, polyacrylic acid and carbopol, peptides and amine acids such as muramyl dipeptide, dimethylglycine, tuftsin and oil emulsions. The polypeptide of the present invention can also be administered following incorporation into liposomes or other micro-carriers, or after conjugation to polysaccharides, other proteins or other polymers or in combination with Quil-A to form "Iscoms" (immunostimulating complexes) (Morein et al., Nature 308, 457-460 [1984]).

The present invention relates also to a method of immunizing a mammal against malaria by treating said mammal with an immunizing amount of the polypeptide or the immunogenic composition described above.

Routes of administration, antigen doses and frequency of injections are all factors which can be optimized using ordinary skill in the art. Typically, the initial vaccination is followed some weeks later by one or more "booster" vaccinations, the net effect of which is the production of high titers of antibodies against the merozoite form of the malaria parasite.

The polypeptides of the present invention or the immunogenic compositions comprising them can be used to induce the formation of antibodies specific for the major merozoite surface antigens of *P. falciparum* in a host. Suitable host animals for eliciting antibodies include mammals such as monkeys, rabbits, horses, goats, guinea pigs, rats, mice, cows, sheep. etc. The resulting antiserum will contain antibodies which will selectively react with and bind to said surface antigen of *P. falciparum*. The antiserum can either be used directly or the specific antibodies can be isolated by methods known in the art, e.g., by ammonium sulfate precipitation. The antiserum or the specific antibodies can be used in a well known manner for diagnostic purposes as well as for purification purposes (e.g., affinity chromatography).

EXAMPLES

Unless otherwise indicated, percentages of liquids in liquids, solids in solid mixtures and solids in liquids are expressed below on a vol/vol, wt/wt and wt/vol basis, respectively.

EXAMPLE 1

Construction of Plasmid pDS6/RBSII,SphI-His,His

A. Principles

Using a chemically synthesized oligonucleotide adaptor, a DNA fragment was inserted behind the RBSII,SphI sequence of the vector pDS8/RBSII,SphI. This fragment encodes an affinity peptide containing two neighbouring histidine residues. A polypeptide containing said affinity peptide may ied by selective mixing to an affinity ography matrix specific for neighbouring histidine es.

Preparation of Synthetic Oligonucleotides

The synthetic oligonucleotides (1) and (2) with the following sequence

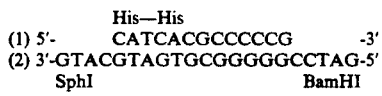

```
           His—His
(1) 5'-    CATCACGCCCCCG         -3'
(2) 3'-GTACGTAGTGCGGGGGCCTAG-5'
    SphI                    BamHI
``` were prepared using controlled pore glass (CPG) as support material (Sproat et al., Tetrahedr. Lett., 24, 5771-5774 [1983]; Adams et al., J. Amer. Chem. Soc., 105, 661-663 [1983]). The lyophilized oligonucleotides were dissolved in water for 1 hour at 4° C and adjusted to a DNA concentration of 100 nmole/ml. 100 pmoles of each oligonucleotide were kinased with 1 μl of [$^{32}$p]-ATP (2 pmoles, 5000 Ci/mmol), 1 unit (U) of T4 polynucleotide kinase (Gibco-BRL, Basle) in 10 μl of 50 mM Tris/HCl (pH 8.5), 10 mM MgCl$_2$, for 10 minutes at 37° C. The reactions were chased by the addition of 1 μl of 5 mM ATP. The reactions were stopped by heating the samples for 7 minutes at 65° C.

C. Construction of pDS6/RBSII,SphI-His,His

4 μg of pDS8/RBSII,SphI were digested with SphI as recommended by the supplier (Gibco-BRL). The enzyme was inactivated by heating the sample for 7 minutes at 65° C., and the DNA was precipitated with 2.5 volumes of ethanol in the presence of 0.3M potassium acetate. The pellet was dried for 2 minutes in a Speed-vac-concentrator and then dissolved in T4 ligase buffer (50 mM Tris/HCl (pH 7.8), 10 mM MgCl$_2$, 10 mM DTT, 500 μM ATP). 50 pmoles of the phosporylated oligonucleotide, comprising the SphI-BamHI-adaptor obtained by hybridizing oligonucleotide (1) to oligonucleotide (2) (see above), dissolved in 1× ligase buffer was added and the volume of the reaction mixture was adjusted to a final volume of 25 μl. The ligation was carried out at 22° C. for 3 hours using 1 μl of DNA-ligase (1 Weiss unit, Boehringer Mannheim). The reaction was stopped by incubating the sample for 7 minutes at 65° C. The DNA was precipitated, dried and Basle) in 10 μl of 50 mM Tris/HCl (pH 8.5). 10 mM MgCl$_2$. 1 then resuspended in restriction buffer (50 mM Tris/HCl (pH 8), 10 mM MgCl$_2$, 50 mM NaCl). After addition of 20 U of BamHI and 10 U of XbaI, the sample was incubated for 1 hour at 37° C. The digestion was stopped by heating the sample for 7 minutes at 65° C.

After the addition of 10× gel sample buffer (100 mM Tris/HCl (pH 8), 0.5% bromphenol-blue, 0.5% xylencyanol, 10 mM EDTA, 50% glycerol), the DNA-fragments were separated in a 6% polyacrylamide gel. The gel wa stained with ethidiniumbromide (1 μg/ml) for 5 minutes, and the DNA was visualized under 300 nm UV-light. Marker DNA was phage φX DNA digested with HaeII (Gibco-BRL, Basle). The DNA band containing the regulatable promoter P$_{N25x/O}$, the ribosomal binding site RBSII,SphI, the annealed adapter, the bla gene and the origin of replication (vector DNA) was cut out of the gel with a scalpel and transferred to a 1.5 ml Eppendorf tube.

Using a pipet tip, the piece of acrylamide containing the DNA band was crushed to a fine granulate. After adding 200 μl of 1× TE-buffer [10 mM Tris/HCl (pH 8.0), 1 mM EDTA] the sample was shaken overnight at 4° C. on a Eppendorf minishaker. The sample was then centrifuged for 15 minutes at 12,000 rpm, the supernatant was transferred into a new Eppendorf tube and the DNA was precipitated with 2.5 volumes of ethanol in the presence of 0.3M potassium acetate. Finally, the DNA was dried under vacuum and resuspended in 10 μl of TE-buffer.

4 μg of plasmid pDS6/RBSII,3A+5A were digested with XbaI and BamHI as recommended by the supplier (BRL-Gibco, Basle). After inactivation of the enzymes (7 minutes, 65° C.), the DNA was precipitated as described above. The pellet was dissolved in 20 μl of 50 mM Tris/HCl (pH 8) containing 2 U of calf intestinal phosphatase (CIP, Boehringer Mannheim) and incubated for 1 hour at 37° C. The reaction was stopped by heating the sample for 7 minutes at 65° C., gel sample buffer was added and the DNA was electrophoretically separated in a 6% polyacrylamide gel. The fragment containing the polylinker, the terminator t$_o$, the cat gene and the terminator T1 was isolated as described above.

The vector DNA and the isolated fragment (0.5 μg each) were ligated in a volume of 30 μl with 2 U of T4 DNA ligase (ligation buffer, 3 hours, 22° C.). The ligation was stopped by heating the sample for 7 minutes at 65° C. The transformation was carried out as described by Morrison (Methods Enzymol. 68, 326-331 [1979]) using as a host *E. coli* M15 harbouring plasmid pDMI,1. The cells were plated on LB-agar plates containing 100 µg/ml ampicillin and 25 µg/ml kanamycin. The plates were incubated overnight at 37° C.

As expected, no transformants were obtained in the control ligation. The ligation containing vector DNA plus the fragment gave about 100 colonies. Single colonies were picked with a tooth pick and grown in 10 ml of LB-medium containing 100 µg/ml ampicillin and 25 µg/ml kanamycin. Plasmid DNA was extracted according to the method of Birnboim et al. (Nucleic Acids Res. 7, 1513-1523 [1979]). The final DNA-pellets were dissolved in 200 µl of TE buffer.

D. Sequence Analysis of pDS6/RBSII,SPhI-His,His

To confirm that the SPhI-BamHI-adaptor is integrated in
pDS6/RBSII,SphI-His,His, the double stranded DNA was sequenced using a primer labeled with [γ-$^{32}$P]-ATP. The primer contains the nucleotides from position 199-218 of pDS8/RBSII,SPhI, and ends therefore 6 nucleotides in front of the ATG of the SphI-site. 15 µl of the isolated DNA (0.3 pmol) were precipitated with ethanol and washed once with 80% ethanol. After drying the pellet for 2 minutes in a Speed-vac-concentrator the pellet was dissolved in 8 µl of ¼ TE-buffer. After the addition of 2 pmol of the primer, end labeled with [γ-$^{32}$P]-ATP, the sample was heated for 5 minutes at 95° C. and then placed for 5 minutes in a 42° C. water bath. Sequencing by the dideoxy-chain-termination method of Sanger et al. (Proc. Natl. Acad. Sci. USA 74, 5463-5467 [1977]) was then carried out.

The sequence data proved that the adaptor is integrated as desired in PDS6/RBSII,SphI-His,His.

EXAMPLE 2

A. Principles

A HpaI-HaeIII fragment (527 bp) was isolated from a clone containing the p190 gene of the K1 isolate of *P. falciparum* (Mackay et al. supra). A BamHI linker was annealed to the blunt ends of this fragment. After digestion with BamHI, the fragment was integrated into expression vector pDS6/RBSII,SphI-His,His which had been linearized with BamHI.

B. Preparation of Fragment 1

6 µg of a clone containing the p190 gene of the K1 isolate of *P. falciparum* were digested with 15 U of HpaI and 25 U of HaeIII in 40 µl of 6 mM NaCl, 6 mM Tris/HCl (pH 7.6), 6 mM MgCl$_2$ for 1 hour at 37° C. After adding 4.5 µl of 10× gel sample buffer (100 mM Tris/HCl (pH 8), 0.5% bromphenol blue, 0.5% xylenecyanol, 10 mM EDTA, 50% glycerol) the DNA fragments were separated in a 6% polyacrylamide gel with 1× TBE (89 mM Tris/HCl (pH 8.0), 89 mM boric acid, 2 mM EDTA) as running buffer for 3 hours at 250 V. The gel was stained with ethidiumbromide (1 µg/ml) for 5 minutes and the DNA was visualized under 300 nm UV-light. Marker DNA was phage φX digested with HaeIII (Gibco-BRL, Basle). The DNA band encoding the desired sequence (527 bp in length) was cut out of the gel and purified as described above.

10 pMoles of a phosphorylated BamHI linker (CCGGATCCGG) were added to the fragment and incubated with 5 U of T4 DNA ligase for 3 hours at 22°

C. The reaction was stopped by heating the sample for 7 minutes at 65° C. After ethanol precipitation, the DNA pellet was resuspended in restriction buffer and digested with 20 U of BamHI for 2 hours at 37° C. in a total volume of 30 µl. After inactivation of the enzyme (7 minutes, 65° C.), gel sample buffer was added and the fragment was isolated after electrophoresis as described above. The final DNA pellet was resuspended in 30 µl of TE-buffer.

C. Preparation of Plasmid pDS6/RBSII,SphI-His,His

4 µg of PDS6/RBSII SphI-His His plasmid DNA were digested for 2 hours at 37° C. with 20 U of BamHI in 30 µl of restriction buffer. After inactivation of the restriction enzyme (7 minutes, 65° C.) the DNA was precipitated as previously described. The pellet was dissolved in 20 µl 50 mM Tris/HCl (pH 8) containing 2 U of calf intestinal phosphatase (CIP, Boehringer Mannheim) and incubated for 1 hour at 37° C. The reaction was stopped by heating the sample for 7 minutes at 65° C. Gel sample buffer was then added, and the DNA was electrophoresed in a 6% polyacrylamide gel. After visualization under UV-light, the vector DNA was cut out of the gel and isolated as described above. The final DNA pellet was resuspended in 20 µl of TE-buffer.

D. Assembly of Plasmid pGC1

10 µl of the vector DNA and half of the isolated fragment 1 were ligated in a volume of 30 µl with 2 U of T4 DNA ligase at 22° C. for 3 hours in ligation buffer. A control ligation with no insert DNA added was done in parallel. The reactions were stopped by heating the samples for 7 minutes at 65° C. Transformations were carried out as described by Morrison (supra) using *E. coli* M15 harbouring plasmid PDMI,1. The cells were plated on LB-agar plates containing 100 µg/ml ampicillin and 25 µg/ml kanamycin. The plates were incubated overnight at 37° C.

As expected, no transformants were obtained in the control ligation. The ligation containing vector DNA plus fragment 1 gave about 200 colonies. Single colonies were picked with a tooth pick and analyzed as described. The plasmid DNA's (5 µl each) were digested in restriction buffer with BamHI to release fragment 1. All plasmids were linearized, but no fragment could be released. This indicated that one BamHI site was lost during the construction (see below).

The plasmids were transformed as described above in *E. coli* M15 harbouring PDMI,1. Single colonies were picked and grown up in 3 ml of LB-medium containing 100 µg/ml ampicillin and 25 µg/ml kanamycin, until the optical density at 600 nm (OD$_{600}$) reached 0.6. A 500 µl sample was removed from the culture (uninduced control), and IPTG was added to the rest to a final concentration of 1 mM. The incubation was continued for 3 hours at 37° C. with shaking (induced samples). A 500 µl sample of the induced and uninduced cultures were centrifuged for 3 minutes at 12,000 rpm. The supernatant was withdrawn and the cell pellet was suspended in SDS gel sample buffer (0.1M Tris/HCl (pH 6.8), 3% β-mercaptoethanol, 20% glycerol, 0.1% bromphenol blue, 3% SDS). The samples were boiled for 5 minutes and placed on ice followed by electrophoresis in a 12.5% polyacrylamide gel (Laemmli, Nature 227, 680-685 [1970]) for 3 hours at 50 mA. The gel was stained for 1 hour with Coomassie blue at room temperature and destained in 10% acetic acid and 10% methanol for 3 hours at 60° C. Half of the colonies analyzed showed a strong band of about 24 kD molecular weight after IPTG-induction. The other half of the colonies had no extra band.

E. Sequence Analysis of pGCI

The nucleotide sequence of the plasmid DNA was determined using primers end labeled with [γ-$^{32}$P]ATP. One primer contained the nucleotides from position 199-218 of pDSB/RBSII,SphI and ends therefore 6 nucleotides in front of the ATG of the SphI site. The other primer contains nucleotides 928-896 of pDS8/RBSII.SphI. In this way fragments integrated into the BamHI site can be sequenced from both directions. The sequence data proved that the p190 fragment was integrated into the BamHI site in frame with the ATG of RBSII,SPhI, but the BamHI site at the end of the fragment was deleted in all constructs.

F. Preparation of the Resin For the Purification of Polypeptides With Neighbouring Histidine Residues 41.7 q of bromoaoetic acid were dissolved in 150 ml of 2N NaOH. The solution was cooled to 0° C., and 42 g of N$^\epsilon$-Z-L-lysine dissolved in 225 ml of 2N NaOH were added dropwise, keeping the temperature at 0° C. After 2 hours, the cooling was stopped and the reaction mixture was kept stirring overnight. The reaction mixture was then kept for 2 hours at 50° C. before 450 ml of 1N HCl were added. The crystals formed after cooling were filtered and recrystallized by first dissolving them in 1N NaOH and then by precipitating them by the addition of an equal volume of 1N HCl. 40 g of N-[5-benzyloxy-carbonylamino-1-carboxy pentyl] iminodiacetic acid in form of white crystals were obtained, melting point (mp) 172°-174° C. (decomposition), $[\alpha]_D = +9.9°$ (concentration=1 g/100 ml; 0.1N NaOH).

7.9 g of the product obtained were dissolved in 49 ml 1N NaOH and hydrated by the addition of 5% Pd/C at room temperature and ambient pressure. The catalysator was removed by filtration and the filtrate was concentrated by evaporation. 6.2 g N-[5-amino-1-carboxypentyl]iminodiacetic acid were obtained.

100 ml of Sepharose TM CL-6B (Pharmacia) were washed twice with 500 ml of H$_2$O. Then 16 ml of 4N NaOH and 8.22 ml of epibromhydrin were added and incubated at 30° C. for 4 hours (total volume 200 ml). The activated Sepharose was washed to neutrality with water and returned to the reaction vessel. 10.6 g of sodium carbonate and 6.2 g of N-[5-amino-1-carboxypentyl]iminodiacetic acid dissolved in 50 ml of H$_2$O were added. The mixture was slowly stirred overnight at 60° C. The resulting NTA-resin of the formula (Sepharose TM CL-6B)—O—CH$_2$—CH(OH)—CH$_2$—N-H—(CH$_2$)$_4$— CH(COOH)—N(CH$_2$COOH)$_2$ was washed with 500 ml of water, then with 100 ml of 2% w/w aqueous NiSO$_4$.6H$_2$O, with 200 ml of H$_2$O, with 200 ml 0.2M acetic acid (containing 0.2M NaCl and 0.1% w/v Tween 20) and finally with 200 ml of H$_2$O. The nickel ion concentration of the resulting NTA resin of the formula [(Sepharose TM CL-6B)—O—CH$_2$—CH(OH)—CH$_2$—NH —(CH$_2$)$_4$ —CH(COOH)—N(CH$_2$COO$^-$)]$_2$Ni$^{2+}$ was 7.1 micromoles/ml.

G. Purification of Polypeptide p190-1

A culture of E. coli M15(pGC1, pDMI,1) was grown for 2 hours at 37° C. with vigorous shaking in LB-medium containing 100 μg/ml ampicillin and 25 μg/ml kanamycin. At an optical density of 0.7 at a wavelength of 600 nm (OD$_{600}$), the expression of the polypeptide p190-1 was induced with IPTG (final concentration 1 mM). After an additional 6 hours of incubation, the cells were harvested by centrifugation.

The harvested cells (46.5 g) were disrupted in 7M guanidine.HCl (140 ml) for 1 hour at 4° C. The soluble proteins were separated from insoluble particles by centrifugation at 10,000× g for 15 minutes at 4° C. The supernatant was diluted five fold with 0.1M Tris/HCl (pH 7.5), 0.2M NaCl and centrifuged as before to yield a crude extract.

The crude extract was applied to the NTA-nickel chelate column described above (Sepharose CL-6B with nitrilotriacetic acid as ligand; column diameter, 5.0 cm, length, 5.5 cm; flow rate, 500 ml/hour). The resin had been equilibrated with 0.1 M Tris/HCl (pH 7.5), 0.2 M NaCl. Contaminating proteins exhibiting poor nickel chelating capacity or lower hydrophobic properties than p190-1 were washed out with 0.1M Tris/HCl (pH 7.5), 0.2M NaCl, then with 0.1M Tris/HCl (pH 6.0), 0.2M NaCl (destruction of low affinity nickel-protein complexes) then with 0.1M Tris/HCl (pH 6.0), 1M (NH$_4$)$_2$SO$_4$ (induction of hydrophobic binding) and finally with 0.1M Tris/HCl (pH 4.5), 1M (NH$_4$)$_2$SO$_4$ (elution of nickel chelate protein complexes which are not bound by hydrophobic interaction). Elution of p190-1 was performed by lowering the (NH$_4$)$_2$SO$_4$ concentration (see FIG. 7). Yield of p190-1: 66 mg, purity ~90%.

The pooled fractions eluted from the NTA-column were diluted 15 fold with H$_2$O and after adjusting the pH value to 6.0, adsorbed on a Fractogel TSK CM-650(M) column (Merck; diameter, 1.6 cm; length, 6.7 cm; flow rate, 1.5 ml/minute; equilibration buffer, 50 mM sodium phosphate (pH 6.0)). p190-1 protein was eluted with a linear gradient of from 0 to 0.6M NaCl for 2 hours. The fractions containing p190-1 were pooled and lyophilized. (Yield ~15 mg, purity ~95%).

Removal of trace amounts of high molecular weight proteins Was accomplished either by preparative HPLC using a Nucleosil 300-S-C18 column (Macherey & Nagel; diameter, 0.4 cm; length, 33 cm; flow rate, 1 ml/minute; equilibration buffer, 0.1% trifluoroacetic acid: elution with a 0-70% gradient of acetonitrile) or by gel filtration on Sephacryl TM S-200 (Pharmacia, diameter, 2.6 cm; length, 81 cm; flow rate, 40 ml/hour, buffer, 1% formic acid). The purified p190-1 protein was recovered after lyophilization as a salt-free powder.

EXAMPLE 3

A. Principles

A 407 bp AluI-BamHI fragment was isolated from a clone containing the p190 gene of the K1 isolate of P. falciparum (Mackay et al., supra). A BamHI linker was annealed to the blunt end of the fragment. After digestion with BamHI, the fragment was integrated into the expression vector pDS6/RBSII,SPhI-His,His which had previously been linearized with BamHI.

B. Preparation of Fragment 2

6 μg of a clone containing the p190 gene of the K1 isolate of P. falciparum were digested with 30 U of AluI and 15 U of BamHI in restriction buffer. After isolation of the fragment and annealing of a BamHI linker (CGGATCCG), the fragment was purified as described above. The final DNA pellet was resuspended in 30 μl of TE buffer.

C. Preparation of Plasmid pDS6/RBSII,SphI-His,His

The preparation of the expression vector is described in Example 2, C.

D. Assembly of Plasmid pGC2

The ligation, transformation and DNA analysis were performed as described in Example 2, D. In four plasmids the BamHI digestion released a fragment of the expected size (410 bp); the other plasmids were only linearized.

E. Sequence Analysis of pGC2

The plasmid DNAs were sequenced as described above. The presence of two different plasmid types was observed. In PGC2a fragment 2 was integrated as expected in the right orientation, in frame with the ATG of the ribosomal binding site RBSII,SPhI and containing BamHI restriction sites at both ends. The other type of plasmids, named pGC2b, contained a small deletion in front of the malaria sequence. In spite of this deletion, the full p190 gene sequence and an affinity peptide containing the neighbouring histidine residues were integrated in these plasmids.

Analysis of the total cellular proteins by SDS-PAGE revealed that all clones containing the p190 sequence in the right orientation and in frame with the ATG of RBSII,SPhI expressed a clearly visible protein of about 20 kD. The plasmid containing the small deletion between RBSII,SphI and the p190 sequence (see above) expressed about 5 times more of this polypeptide, compared to the constructs without the deletion. The polypeptide derived from pGC2a was named p190-2a, and the polypeptide derived from pGC2b was named p190-2b.

As outlined above, plasmid pGC2b containing the small deletion was obtained by chance through a deletion mutation. A plasmid like PGC2b can also be produced from plasmid PGC2a by primer-directed mutagenesis (Morinaga et al., Bio/Technology 7, 636–639 [1984]) using a small synthetic oligonucleotide primer comprising the nucleotide sequence adjacent to the desired deletion but lacking the nucleotides to be deleted.

F. Purification of Polypeptide p190-2b

Polypeptide p190-2b was purified by analogy to the purification of p190-1 described in Example 2. *E. coli* cells (16.6 g) were disrupted in 50 ml of 7M guanidine.HCl, and the crude extract was applied to an NTA-nickel chelate column (diameter 2.6 cm, length 8.8 cm, flow rate 160 ml/hour), yielding 14 mg of p190-2b with a purity of ~90%.

The pooled fractions eluted from the NTA-column were diluted 15 fold with $H_2O$ and, after adjusting the pH to 7.5, adsorbed on a Fractogel TSK DEAE-650(M) ® column (Merck; diameter, 1.6 cm; length. 8.8 cm; flow rate, 120 ml/hour, equilibration buffer, 25 mM Tris/HCl (pH 7.5)). p190-2b was eluted with a linear gradient of from 0 to 0.6M NaCl for 3 hours. The fractions containing p190-2b were pooled and lyophilized. Yield: 9 mg, purity >95%.

Final purification was performed with preparative HPLC as described in Example 2, using a RP-18 column (Macherey & Nagel, diameter 10 mm, length 250 mm, flow rate 5 ml/minute, elution with a gradient of acetonitrile, sample load 2-5 mg of DEAE-pool). Yield: ~5 mg.

Polypeptide p190-2a can be similarly purified.

EXAMPLE 4

A. Principles

The BamHI fragment (fragment 3) with the sequence derived from the p190 gene was isolated from PGC2a, which contains both BamHI restriction sites. This fragment was integrated into the BamHI-digested vector PGCl, resulting in plasmid pGC3 expressing a fusion polypeptide.

B. Preparation of Fragment 3

4 μg of plasmid pGC2a were digested with 15 U of BamHI (restriction buffer, 20 μl volume, 1 hour, 37° C.). After heat inactivation of the enzyme (7 minutes, 65° C.), the fragment was isolated as described above. The final pellet was resuspended in 20 μl of TE-buffer.

C. Preparation of plasmid pGC1

4 μg of plasmid PGCl were digested with 15 U of BamHI. The DNA was precipitated and treated with calf intestinal phosphatase as described above. The linearized plasmid DNA was purified from a 6% preparative polyacrylamide gel (see above). The final DNA pellet was resuspended in 10 μl of TE-buffer.

D. Assembly of pGC3

Plasmid PGCl linearized with BamHI (vector DNA) was ligated with 10 μl of isolated fragment 3 (2 U of T4-DNA-ligase, ligation buffer, 3 hours, 22° C., 30 μl volume). A control ligation with no insert DNA added was done in parallel. The ligations were stopped by heating the samples for 7 minutes at 65° C. Transformations were carried out as described by Morrison (supra). The ligation containing vector DNA plus fragment 3 gave about 50 colonies. Analysis of the colonies was performed as described above. The plasmid DNA was digested with BamHI. Of the plasmids which were analyzed, ten contained a BamHI fragment of about 400 bp.

E. Sequence Analysis of plasmid pGC3 and Expression of polypeptide p190-3

The DNA sequence of 4 plasmids was determined as previously described. One plasmid contained the BamHI fragment in the right orientation. Sequence analysis proved that fragment 3 and fragment 1 were fused in the same translational reading frame. The plasmid was named pGC3. The analysis of induced cultures using SDS PAGE showed that clones containing pGC3 produced a 40,000 Dalton protein in high amount. For details, see FIG. 9.

F. Purification of Polypeptide p190-3

Bacterial pellets containing P190-3 were suspended in 0.01M Hepes (pH 7.8) 0.01M $MgSO_4$. 0.15M NaCl, 10% Glycerol to about $4 \times 10^{10}$ cells per ml. DNase I and the protease inhibitor, Trasylol ™ (Bayer), were added to concentrations of 1 μg/ml and 100 units/ml, respectively.

Bacterial cells were broken in a French pressure cell at 20,000 $lb/in^2$ (~$1.379 \times 10^8$ pascal). Cell lysis was monitored by phase contrast microscopy and was found to be greater than 98%.

A crude lysate was obtained by differential centrifugation at 2,000 rpm (480× g) for 15 minutes, 8,000 rpm (8,000× g) for 15 minutes, 15,000 rpm (20,000× g) for 15 minutes and 42,000 rpm (150,000× g) for 60 minutes.

The distribution of p190-3 in the various fractions was determined by polyacrylamide gel electrophoresis in the presence of SDS (SDS PAGE), and by immunoblotting.

More than 80% of the p190-3 was found in the 8,000 rpm and 15,000 rpm pellets. The 2,000 rpm pellet contained bacterial debris the 42,000 rpm pellet contained bacterial membranes and the 42,000 rpm supernatant contained bacterial cytoplasmic proteins. The 8,000 and 15,000 rpm pellets were suspended in 25 mM imidazole-HCl (pH 7.5) containing 10% glycerol, 5 mM EDTA and 5 mM DTT, with the help of a small magnet. An equal volume of 6M area, prepared in the same buffer, was added. The suspension was centrifuged at 15,000 rpm (20,000× g) for 15 minutes. This extraction step solubilized some of the bacterial contaminants, leaving the p190-3 in the pellet.

This pellet was then solubilized in 9M urea prepared in 25 mM imidazole-HCl (pH 7.5), 10% glycerol, 5 mM EDTA and 5 mM DTT. The solution was centrifuged at 42,000 rpm (150,000× g) for 60 minutes and applied atop a chromatofocusing column (PBE 94, Pharmacia), equilibrated with 9M urea in 25 mM imidazole-HCl, pH 7.5. Unbound material was washed out of the column with equilibration buffer, and the p190-3 was eluted with polybuffer 74-HCl (Pharmacia), pH 4.0, diluted 1:8 with water and containing 9M urea.

Distribution of p190-3 in the column fractions was assessed by SDS PAGE. Fractions containing p190-3 were pooled and precipitated by the addition of saturated ammonium sulfate, $(NH_4)_2SO_4$, to 65% saturation. The mixture was left on ice for 2 hours and the precipitate was collected by centrifugation at 10,000 rpm (12,000× g) for 15 minutes. The pellet was solubilized in 1 mM sodium phosphate buffer (pH 6.8), containing 4M guanidine-HCl.

The solution was dialyzed against 1 mM sodium phosphate buffer, pH 6.8, 4M guanidine-HCl for 16 hours at 4° C. The dialysate was centrifuged at 42,000 rpm for 60 minutes and the supernatant fraction was applied to a hydroxylapatite column (HA-Ultragel, LKB), equilibrated with 1 mM sodium phosphate buffer (pH 6.8) and containing 4M guanidine-HCl. Unbound material was washed through the column with equilibration buffer and p190-3 was eluted with a linear gradient of 0-0.4M potassium phosphate buffer (pH 6.8) containing 4M guanidine-HCl, at a flow rate of 0.2 ml per minute.

Distribution of p190-3 in the column fractions was assessed by SDS PAGE. Since guanidine-HCl forms an insoluble precipitate with SDS, an aliquot of each peak fraction was first precipitated with trichloroacetic acid (TCA) (10% final conc.). The precipitates were centrifuged in an Eppendorf centrifuge for 3 minutes and the pellets were washed free of TCA by resuspension and centrifugation in acetone.

Fractions from the HA-Ultragel column that contained p190-3 were pooled and precipitated with $(NH_4)_2SO_4$ at 65% saturation as described above. The precipitated protein was centrifuged and the pellet was resuspended in saline (0.9% NaCl). Since p190-3 is not soluble in saline, but $(NH_4)_2SO_4$ is, an additional centrifugation step extracted the $(NH_4)_2SO_4$, leaving pure p190-3 in the pellet. An immunoblot (Western-blot, Towbin et al., Proc. Natl. Acad. Sci. U.S.A. 76, 4350-4354 [1979]) showed that p190-3 reacted not only With a rabbit polyclonal antiauthentic p190 antiserum but also with monoclonal mouse anti-p190-1 and anti-p190-2b antibodies.

Polypeptide p190-3 was further purified by preparative SDS-PAGE (Takacs. Immunol. Methods 1. 81-105 [1979]). The result of such a purification is shown in FIG. 9. The analytical SDS-PAGE of purified p190-3 under reducing (sample buffer containing 5% $\beta$-mercaptoethanol) and nonreducing (sample buffer without $\beta$-mercaptoethanol) conditions showed that in the absence of $\beta$-mercaptoethanol, p190-3 readily forms dimers, trimers and tetramers, which could account for its insolubility in most aqueous buffers.

The saline washed, ammonium sulfate precipitated p190-3 pellet described above, was used as immunogen for the production of antisera. The pellet was resuspended in saline with the help of a glass-Teflon homogenizer. The suspension was then mixed with complete Freund's adjuvant (CFA) or adsorbed to aluminum hydroxide prior to injection.

EXAMPLE 5

Immunogenicity Data for p190-1, p190-2b and p190-3

Single colonies of *E. coli* M15 transformed with either PGC1, pGC2b or pGC3 were transferred to a tube containing 10 ml of LB medium with 100 $\mu$g/ml ampicillin and 25 $\mu$g/ml kanamycin, and grown for 12 hours at 37° C. with vigorous shaking. At an optical density of 0.7 at a wavelength of 600 nm (OD600). the cultures were induced with IPTG (final concentration 1 mM). After an additional 6 hours of incubation, the cells were harvested by centrifugation.

Cells isolated from a volume of 40 $\mu$l of culture medium were resuspended in sample buffer containing 3% sodium dodecyl sulfate (SDS), 3% $\beta$-mercaptoethanol, 20% glycerol and 125 mM Tris/HCl (pH 6.8). The samples were boiled for 5 minutes, chilled on ice, centrifuged at 12,000× g for 30 seconds and electrophoresed in an SDS-polyacrylamide gel (12.5% acrylamide, ratio of acrylamide/bisacrylamide 30/0.8) according to the procedure of Laemmli (supra).

The polypeptides of the cell extract separated by SDS-polyacrylamide gel electrophoresis (3 hours, 30 mA) were then transferred to nitrocellulose filter paper by the Western blot-technique (Towbin et al., supra). After the transfer, the filter was rinsed for 10 minutes in 1× TBS (50 mM Tris/HCl (pH 7.4), 150 mM NaCl) followed by a 30 minutes incubation in 1× TBS, 5% fat-free milk powder. The filter was then incubated for 2 hours with rabbit anti-p190 serum (1:1000 dilution in 1 x TBS, 5% fat-free milk powder). Unbound antibodies were removed by five washes with 1× TBS. The filter was then incubated with the second antibody for 1 hour (goat anti-rabbit coupled to horseradish peroxidase [Biorad], 1:1000 dilution in 1× TBS, 5% fat-free milk powder).

After the incubation, the filter was washed five times in 1× TBS. The filter was placed in 50 ml of 1× TBS, and 10 ml of a 4-chloronaphtol solution (Sigma, 4 mg/ml in methanol) were added. After adding 50 $\mu$l of hydrogen peroxide, bands reacting with the antiserum became visible. As shown in FIG. 10, panel A, lanes 1-3, rabbit serum raised against the native parasite p190 protein reacts specifically with a single band in each lane. This band comigrates with a strong band visible in an SDS polyacrylamide gel done in parallel with the same samples and stained with Coomassie brilliant Blue R-250 (FIG. 10, panel C). The recombinant polypeptides had the expected molecular weights.

In a second Western blot, pooled human malaria sera from endemic areas were used. Again, the same bands gave a strong signal even at a serum dilution of 1:2000 (FIG. 10, panel B), indicating that p190-1 (lane 1) and p190-3 (lane 3) contain a major epitope of the 190 kD precursor to the major merozoite surface antigens of *P. falciparum*.

Unlike p190-1 and p190-3, polypeptide p190-2b did not react with human malaria sera from endemic areas (FIG. 10, panel B, lane 2). This might be explained if the epitope represented by p190-2b is located closely to the membrane anchor of p190 and might, therefore, not be exposed to the human immune system. Rabbit serum against native p190 reacts with that epitope. This might be because the animals were immunized with unfolded p190 and not due to the absence of an epitope on that particular polypeptide. Of course, understanding the actual reason for the foregoing observations is not essential to this invention.

The results of the Western-blot were confirmed by an ELISA test using rabbit anti-p190 serum. (Table I). The negative controls, bovine serum albumin (BSA) and a lysate of an *E. coli* bacterium expressing high amounts of a non-malaria related recombinant protein, gave O.D. readings of 0.01 and 0.02, respectively. The positive control, native p190 protein isolated from parasites, gave a value of 0.13. Bacterial lysates of *E. coli* M15(PGC1; PDMI,1) and *E. coli* M15(pGC2b; PDMI,1) gave values of 0.15 and 0.13, respectively, which are comparable to the value of the native p190 protein (positive control), which was 0.13. This suggested that the recombinant polypeptides p190-1 and p190-2b carry some important epitopes of the p190 protein.

TABLE I

| ELISA-analysis of p190-1 and p190-2b | |
|---|---|
| Sample | O.D.$^{450}$ |
| Bovine Albumin | 0.01 |
| *E. coli* M15/pMF-1 | 0.02 |
| Native p190 Protein | 0.13 |
| *E. coli* M15(pGCl:pDMI,1) | 0.15 |
| *E. coli* M15(pGC2:pDMI,1) | 0.13 |

Antigens were detected using anti-p190 rabbit serum (dilution 1:2000). 10 ng of BSA and p190 were used for coating the plates. The bacterial lysates contained about 1 µg total protein. Dilution curves were made for each sample to obtain optimal coating concentrations.

In a further experiment, Balb/c mice were immunized with two subcutaneous injections, 1 month apart, of about 50 µg of p190-1 or 200 µg of p190-2b. The first injection was made in complete Freuend's adjuvant, the second in incomplete Freund's adjuvant. A third injection of 50 µg of antigen in incomplete adjuvant was given 1 month (p190-1) or two weeks (p190-2b) after the second injection. Three days (p190-1) or 4 days (p190-2b) later, serum was taken and assayed for reaction with the purified polypeptides p190-1, p190-2b or p190-3 by ELISA assay, or with fixed *P. falciparum* blood stage parasites of various isolates by indirect immunofluorescence.

For the ELISA test, plates were coated with antigen (1 µg/ml in 0.14M NaCl), and blocked with bovine serum albumin (10 mg/ml in 0.1M borate, 0.14M NaCl, pH 8.4) Serum samples (ten-fold dilutions) were added for 2 hours. The plate was washed with borate/saline buffer, and antibody binding after the wash was detected with alkaline phosphatase-coupled rabbit anti-mouse Ig (Sigma) according to the manufacturer's instructions. Table II shows that p190-1 and p190-2b are immunogenic in Balb/c mice, that antiserum to p190-1 does not cross-react significantly with p190-2b (or vice versa) and that both anti-p190-1 and anti-p190-2b react with p190-3.

TABLE II

| | Polypeptide | | |
|---|---|---|---|
| Serum | p190-1 | p190-2b | p190-3 |
| Anti p190-1 | $10^4$ (0.28) | $10^2$ (0.22) | $10^6$ (0.37) |
| Anti p190-2b | $10^2$ (0.11) | $>10^6$ (1.6) | $10^6$ (0.25) |

Table II shows ELISA titers of mouse anti-p190-1 and anti-p190-2b on fragments p190-1, p190-2b and p190-3. Numbers in brackets are the corresponding optical density readings at that titer. Optical densities of <0.1 are considered negative.

For the immunofluorescence assay, drop preparations of *P. falciparum*-infected erythrocytes were prepared from asynchronous cultures of the parasite. The air-dried slides (12 drops per slide) were stored at −20° C. Just before use, the slides were fixed with acetone. The parasites were then reacted for 20 minutes at 37° C. with the test sera. The slides were washed in PBS, fluorescein-conjugated goat anti-mouse Ig antiserum was added and the samples were incubated for another 20 minutes. The slides were then washed, mounted in glycerol (50% in phosphate-buffered saline) and examined under UV light. The following *P. falciparum* isolates were examined: Kl, MAD-20, FCH-5, Ro-33, Ro-58. All isolates stained positively with sera (diluted 1/100) from the mice immunized with either p190-1 or p190-2b.

Many modifications and variations of this invention may be made without departing from its spirit and scope, as will be apparent to those skilled in the art. The specific embodiments described herein are offered by way of example only, and the invention is limited only by the terms of the appended claims.

What is claimed is:

1. An isolated DNA sequence wherein said sequence is as follows:

```
ATG CAT CAC GCC CCC GGA TCC GGA ACT TTG TGT GAT AAT ATT CAT
GGT TTC AAA TAT TTA ATT GAT GGA TAT GAA GAA ATT AAT GAA TTA
TTA TAT AAA TTA AAC TTT TAT TTT GAT TTA TTA AGA GCA AAA TTA
AAT AAT GTA TGT GCT AAT GAT TAT TGT CAA ATA CCT TTC AAT CTT
AAA ATT CGT GCA AAT GAA TTA GAC GTA CTT AAA AAA CTT GTG TTC
GGA TAT AGA AAA CCA TTA GAC AAT ATT AAA GAT AAT GTA GGA AAA
ATG GAA GAT TAC ATT AAA AAA AAT AAA AAA ACC ATA GAA AAT ATA
AAT GAA TTA ATT GAA GAA AGT AAG AAA ACA ATT GAT AAA AAT AAG
AAT GCA ACT AAA GAA GAA GAA AAA AAA AAA TTA TAC CAA GCT CAA
TAT GAT CTT TTT ATT TAC AAT AAA CAA TTA GAA GAA GCA CAT AAT
TTA ATA AGC GTT TTA GAA AAA CGT ATT GAC ACT TTA AAA AAA AAT
GAA AAC ATT AAG GAA TTA CTT GAT AAG ATA AAT GAA ATT AAA AAT
```

-continued

```
CCC CCA CCG GCC GGT GGA CTC CTG TTG ATA GAT CCA GTA ATG ACC
TCA GAA CTC CAT CTG GAT TTG TTC AGA ACG CTC GGT TGC CGC CGG
GCG TTT TTT ATT GGT GAG AAT CCA AGC TAG.
```

2. An isolated DNA sequence wherein said sequence is as follows:

```
ATG CAT CAC GCC CCC GGA TCC GCT GAA ATA GCA GAA ACT GAA AAC
ACA TTA GAA AAC ACA AAA ATA TTA TTG AAA CAT TAT AAA GGA CTT
GTT AAA TAT TAT AAT GGT GAA TCA TCT CCA TTA AAA ACT TTA AGT
GAA GAA TCA ATT CAA ACA GAA GAT AAT TAT GCC AGT TTA GAA AAC
TTT AAA GTA TTA AGT AAA TTA GAA GGA AAA TTA AAG GAT AAT TTA
AAT TTA GAA AAG AAA AAA TTA TCA TAC TTA TCA AGA GGT TTA CAT
CAT TTA ATT GCT GAA TTA AAA GAA GTA ATA AAA AAT AAA AAT TAT
ACA GGT AAT TCT CCA AGC GTA AAT AAT ACG GAT GTT AAC AAT GCA
TTA GAA TCT TAC AAA AAA TTT CTC CCA GAA GGA ACA GAT GTT GCA
ACA GTT GTA AGT GAA AGT GGA TCC GTC GAC CTG CAG CCA AGC TTG
GAC TCC TGT TGA.
```

3. An isolated DNA sequence wherein said sequence is as follows:

```
ATG CAT CAC GCC CCC GCT GAA ATA GCA GAA ACT GAA AAC ACA TTA
GAA AAC ACA AAA ATA TTA TTG AAA CAT TAT AAA GGA CTT GTT AAA
TAT TAT AAT GGT GAA TCA TCT CCA TTA AAA ACT TTA AGT GAA GAA
TCA ATT CAA ACA GAA GAT AAT TAT GCC AGT TTA GAA AAC TTT AAA
GTA TTA AGT AAA TTA GAA GGA AAA TTA AAG GAT AAT TTA AAT TTA
GAA AAG AAA AAA TTA TCA TAC TTA TCA AGA GGT TTA CAT CAT TTA
ATT GCT GAA TTA AAA GAA GTA ATA AAA AAT AAA AAT TAT ACA GGT
AAT TCT CCA AGC GTA AAT AAT ACG GAT GTT AAC AAT GCA TTA GAA
TCT TAC AAA AAA TTT CTC CCA GAA GGA ACA GAT GTT GCA ACA GTT
GTA AGT GAA AGT GGA TCC GTC GAC CTG CAG CCA AGC TTG GAC TCC
TGT TGA.
```

4. An isolated DNA sequence wherein said sequence is as follows:

```
ATG CAT CAC GCC CCC GGA TCC GCT GAA ATA GCA GAA ACT GAA AAC
ACA TTA GAA AAC ACA AAA ATA TTA TTG AAA CAT TAT AAA GGA CTT
GTT AAA TAT TAT AAT GGT GAA TCA TCT CCA TTA AAA ACT TTA AGT
GAA GAA TCA ATT CAA ACA GAA GAT AAT TAT GCC AGT TTA GAA AAC
TTT AAA GTA TTA AGT AAA TTA GAA GGA AAA TTA AAG GAT AAT TTA
AAT TTA GAA AAG AAA AAA TTA TCA TAC TTA TCA AGA GGT TTA CAT
CAT TTA ATT GCT GAA TTA AAA GAA GTA ATA AAA AAT AAA AAT TAT
ACA GGT AAT TCT CCA AGC GTA AAT AAT ACG GAT GTT AAC AAT GCA
TTA GAA TCT TAC AAA AAA TTT CTC CCA GAA GGA ACA GAT GTT GCA
ACA GTT GTA AGT GAA AGT GGA TCC GGA ACT TTG TGT GAT AAT ATT
CAT GGT TTC AAA TAT TTA ATT GAT GGA TAT GAA GAA ATT AAT GAA

TTA TTA TAT AAA TTA AAC TTT TAT TTT GAT TTA TTA AGA GCA AAA
TTA AAT AAT GTA TGT GCT AAT GAT TAT TGT CAA ATA CCT TTC AAT
CTT AAA ATT CGT GCA AAT GAA TTA GAC GTA CTT AAA AAA CTT GTG
TTC GGA TAT AGA AAA CCA TTA GAC AAT ATT AAA GAT AAT GTA GGA
AAA ATG GAA GAT TAC ATT AAA AAA AAT AAA ACC ATA GAA AAT
ATA AAT GAA TTA ATT GAA GAA AGT AAG AAA ACA ATT GAT AAA AAT
AAG AAT GCA ACT AAA GAA GAA GAA AAA AAA AAA TTA TAC CAA GCT
CAA TAT GAT CTT TTT ATT TAC AAT AAA CAA TTA GAA GAA GCA CAT
AAT TTA ATA AGC GTT TTA GAA AAA CGT ATT GAC ACT TTA AAA AAA
AAT GAA AAC ATT AAG GAA TTA CTT GAT AAG ATA AAT GAA ATT AAA
AAT CCC CCA CCG GCC GGT GGA CTC CTG TTG ATA GAT CCA GTA ATG
ACC TCA GAA CTC CAT CTG GAT TTG TTC AGA ACG CTC GGT TGC CGC
CGG GCG TTT TTT ATT GGT GAG AAT CCA AGC TAG.
```

5. An isolated DNA sequence coding for the following amino acid sequence:

ThrLeuCysAspAsnIleHisGlyPheLysTyrLeuIleAspGlyTyrGlu
GluIleAsnGluLeuLeuTyrLysLeuAsnPheTyrPheAspLeuLeuArg
AlaLysLeuAsnAsnValCysAlaAsnAspTyrCysGlnIleProPheAsn
LeuLysIleArgAlaAsnGluLeuAspValLeuLysLysLeuValPheGly
TyrArgLysProLeuAspAsnIleLysAspAsnValGlyLysMetGluAsp
TyrIleLysLysAsnLysLysThrIleGluAsnIleAsnGluLeuIleGlu
GluSerLysLysThrIleAspLysAsnLysAsnAlaThrLysGluGluGlu
LysLysLysLeuTyrGlnAlaGlnTyrAspLeuPheIleTyrAsnLysGln
LeuGluGluAlaHisAsnLeuIleSerValLeuGluLysArgIleAspThr
LeuLysLysAsnGluAsnIleLysGluLeuLeuAspLysIleAsnGluIle
LysAsnProProPro.

6. The DNA sequence of claim 5 wherein said sequence is directly linked and in proper reading frame with a DNA sequence coding for an affinity peptide residue.

7. An isolated DNA sequence coding for the following amino acid sequence:

AlaGluIleAlaGluThrGluAsnThrLeuGluAsnThrLysIleLeuLeu
LysHisTyrLysGlyLeuValLysTyrTyrAsnGlyGluSerSerProLeu
LysThrLeuSerGluGluSerIleGlnThrGluAspAsnTyrAlaSerLeu
GluAsnPheLysValLeuSerLysLeuGluGlyLysLeuLysAspAsnLeu
AsnLeuGluLysLysLysLeuSerTyrLeuSerArgGlyLeuHisHisLeu
IleAlaGluLeuLysGluValIleLysAsnLysAsnTyrThrGlyAsnSer
ProSerValAsnAsnThrAspValAsnAsnAlaLeuGluSerTyrLysLys
PheLeuProGluGlyThrAspValAlaThrValValSerGluSerGlySer.

8. The DNA sequence of claim 7 wherein said sequence is directly linked and in proper reading frame with a DNA sequence coding for an affinity peptide residue.

9. An isolated DNA sequence coding for the following amino acid sequence:

ThrLeuCysAspAsnIleHisGlyPheLysTyrLeuIleAspGlyTyrGlu
GluIleAsnGluLeuLeuTyrLysLeuAsnPheTyrPheAspLeuLeuArg
AlaLysLeuAsnAsnValCysAlaAsnAspTyrCysGlnIleProPheAsn
LeuLysIleArgAlaAsnGluLeuAspValLeuLysLysLeuValPheGly
TyrArgLysProLeuAspAsnIleLysAspAsnValGlyLysMetGluAsp
TyrIleLysLysAsnLysLysThrIleGluAsnIleAsnGluLeuIleGlu
GluSerLysLysThrIleAspLysAsnLysAsnAlaThrLysGluGluGlu
LysLysLysLeuTyrGlnAlaGlnTyrAspLeuPheIleTyrAsnLysGln
LeuGluGluAlaHisAsnLeuIleSerValLeuGluLysArgIleAspThr
LeuLysLysAsnGluAsnIleLysGluLeuLeuAspLysIleAsnGluIle
LysAsnProProPro

AlaGluIleAlaGluThrGluAsnThrLeuGluAsnThrLysIleLeuLeu

-continued
LysHisTyrLysGlyLeuValLysTyrTyrAsnGlyGluSerSerProLeu
LysThrLeuSerGluGluSerIleGlnThrGluAspAsnTyrAlaSerLeu
GluAsnPheLysValLeuSerLysLeuGluGlyLysLeuLysAspAsnLeu
AsnLeuGluLysLysLysLeuSerTyrLeuSerArgGlyLeuHisHisLeu
IleAlaGluLeuLysGluValIleLysAsnLysAsnTyrThrGlyAsnSer
ProSerValAsnAsnThrAspValAsnAsnAlaLeuGluSerTyrLysLys
PheLeuProGluGlyThrAspValAlaThrValValSerGluSerGlySer.

10. The DNA sequence of claim 9 wherein said sequence is directly linked and in proper reading frame with a DNA sequence coding for an affinity peptide residue.

11. A recombinant vector comprising the DNA sequence of claim 9, wherein said DNA sequence is operably linked to a promoter sequence which is capable of directing the expression of the DNA sequence in a host microorganism.

12. A microorganism transformed with the recombinant vector of claim 11.

* * * * *